(12) United States Patent
Peltier-Pain et al.

(10) Patent No.: US 9,816,122 B2
(45) Date of Patent: Nov. 14, 2017

(54) GLYCOCONJUGATE SYNTHESIS

(71) Applicant: Glycom A/S, Kongens Lyngby (DK)

(72) Inventors: Pauline Peltier-Pain, Orleans (FR); Gyula Dekany, Sinnamon Park (AU); Christophe Pain, Fleury-les-Aubrais (FR); Pierre Chassagne, Beaumont (FR); Nicolas Fierfort, Varangeville (FR); Dóra Molnàr-Gàbor, Budapest (HU)

(73) Assignee: Glycom A/S, Kongens Lyngby (DK)

( * ) Notice: Subject to any disclaimer, the term of this patent is extended or adjusted under 35 U.S.C. 154(b) by 0 days.

(21) Appl. No.: 14/430,930

(22) PCT Filed: Sep. 25, 2013

(86) PCT No.: PCT/DK2013/050306
§ 371 (c)(1),
(2) Date: Mar. 25, 2015

(87) PCT Pub. No.: WO2014/048439
PCT Pub. Date: Apr. 3, 2014

(65) Prior Publication Data
US 2015/0252400 A1 Sep. 10, 2015

(30) Foreign Application Priority Data

Sep. 25, 2012 (DK) .................................. 2012 70582
Jun. 7, 2013 (DK) .................................. 2013 70311

(51) Int. Cl.
| | | |
|---|---|---|
| *C12P 19/18* | (2006.01) | |
| *C12P 19/44* | (2006.01) | |
| *C07H 15/08* | (2006.01) | |
| *C07H 13/04* | (2006.01) | |
| *C07H 15/04* | (2006.01) | |
| *C07H 15/26* | (2006.01) | |

(52) U.S. Cl.
CPC ............. *C12P 19/44* (2013.01); *C07H 13/04* (2013.01); *C07H 15/04* (2013.01); *C07H 15/08* (2013.01); *C07H 15/26* (2013.01); *C12P 19/18* (2013.01)

(58) Field of Classification Search
CPC ...................................................... C12P 19/18
See application file for complete search history.

(56) References Cited

U.S. PATENT DOCUMENTS

| 7,521,212 B1 | 4/2009 | Samain et al. |
| 2009/0082307 A1* | 3/2009 | Samain ................... C07H 3/06 514/54 |
| 2012/0208181 A1 | 8/2012 | Merighi et al. |

FOREIGN PATENT DOCUMENTS

| EP | 1911850 | 4/2008 |
| WO | WO0104341 | 1/2001 |
| WO | WO2007101862 | 9/2007 |
| WO | WO2008002230 | 1/2008 |
| WO | WO2009040363 | 4/2009 |
| WO | WO2010070104 | 6/2010 |

OTHER PUBLICATIONS

S.G. Olsen et al. "Analysis of the Structural Specificty of the Lactose Permease Toward Sugars", J. Biol. Chem. 254(27):15982-15987 (1989).*
Fort, S. et al, "Biosynthesis of conjugatable saccharidic moieties of GM2 and GM3 gangliosides by engineered *E. coli*", Chem Commun, pp. 2558-2560, (2005).
Drouillard, S. et al, "Large-scale synthesis of H-Antigen Oligosaccharides by expressing helicobacter pylori alpha 1,2-Fucosyltransgerase in metabolically engineered *Escherichia coli* cells", Angewandte Chem. Int. Ed., vol. 45, pp. 1778-1780, (Feb. 14, 2006).
Sugihara, J. et al, "Sugar recognition by CscB and LacY", Biochemistry, vol. 50, pp. 11009-11014, (2011).
Samain, E. et al, "Production of O-acetylated and sulfated chitooligosaccharides by recombinant *Escherichia coli* strains harboring different combinations of nod genes", Journal of Biotechnology, vol. 72, pp. 33-47, (1999).
Kallin, E. et al, "Derivatization procedures for reducing Oligosaccharides, Part 3: Preparation of oligosaccharide glycosylamines, and their conversion into oligosaccharides-acrylamide copolymers", J. Carbohydrate Chemistry, 8:4:597-611, (1989).
Meloncelli, P. et al, "Synthesis of ABO histo-blood group type V and VI antigens", Aust. J. Chem., vol. 62, pp. 558-574 (2009).
Rude, E. et al, "Synthesis of the N-carboxy-alpha-amino acid anhydrides of several O-acetylated serine glycosides", Carbohydrate Research, vol. 8, pp. 219-232, (1968).
S. DeFrees et al, "GlycoPEGylation of recombinant therapeutic proteins produced in *Escherichia coli*", Glycobiology, 16(9):833-843 (2006).

* cited by examiner

*Primary Examiner* — Rebecca Prouty
(74) *Attorney, Agent, or Firm* — McHale & Slavin, P.A.

(57) ABSTRACT

The invention relates to a method for producing a glycoconjugate comprising an oligosaccharide part covalently linked to a non-sugar moiety selected from the group consisting of amino acids, peptides, proteins, lipids, longer alkyl groups, polyethylene glycols, α,β-unsaturated amido group and polyvinyl alcohols, using a genetically modified cell.

14 Claims, No Drawings

GLYCOCONJUGATE SYNTHESIS

CROSS REFERENCE TO RELATED APPLICATIONS

This is a national stage filing in accordance with 35 U.S.C. §371 of PCT/DK2013/050306, filed Sep. 25, 2013, which claims the benefit of the priority of Denmark Patent Application No. PA 2012 70311, filed Jun. 7, 2013 and Denmark Patent Application No. PA 2012 70582, filed Sep. 25, 2012 the contents of each are incorporated herein by reference.

FIELD OF THE INVENTION

The present invention relates to a method of making glycoconjugates using genetically modified cells.

BACKGROUND OF THE INVENTION

In general, glycoconjugates are carbohydrate derivatives in which the carbohydrate part is linked to another chemical moiety by covalent linkage. Glycoconjugates like glycoproteins, glycopeptides, peptidoglycans, glycolipids, lipopolysaccharides play important roles in living systems, particularly in cell-cell or cell-matrix interactions.

Glycoproteins are proteins that contain sugar moiety/moieties, particularly oligosaccharide chain(s), covalently attached to the amino acid unit(s) of the polypeptide chain of a protein, preferably via the OH-group of an amino acid (serine, threonine, hydroxyproline) or the amide nitrogen of asparagine or glutamine (O- vs. N-glycosides). Glycoproteins are often parts of cell membranes. Glycopeptides are similar to glycoproteins in that the glycosyl moiety is attached to an amino acid, but that particular amino acid can be a single aglycon or the part of an oligopeptide.

Glycolipids are lipid (fatty acid) containing carbohydrate conjugates, generally classified in the groups of glyceroglycolipids, glycosphingolipids and glycosylphosphatidylinositols, with the role providing energy for the cell. Lipopolysaccharides, also lipid containing glycoconjugates, but having antennary-like polysaccharide chains, are components of the outer membrane of bacteria and involved in inducing immune response.

Preparing complex molecules such as glycoconjugates has always been a challenge for chemists and biologists. Structurally altered analogues of glycopeptides can be important targets in studying and understanding basic physiological processes taking place in cell systems. Glycoconjugates and analogues thereof can be synthesized by both chemical and enzymatic ways. In chemical synthesis, the carbohydrate part has been reacted with the aglycon under glycosylation condition, in which both the participating educts shall be present in protected form, that is all functional groups that are not involved in forming the desired linkage and can be affected under glycosylation conditions shall be masked. This chemical approach, in many cases, can suffer from low stereoselectivity with regard to the newly formed glycosidic bond, low overall yield due to the high number of protection/deprotection steps, the use of sophisticated and often expensive purification methodologies such as column chromatography, and sometimes the use of toxic reagents. Alternatively, enzyme mediated glycosylation reactions can require fewer or even just a few elementary steps and/or take place with remarkable stereo- and/or regioselectivity, but the narrow substrate specificity of the enzymes towards the donors and the acceptors often requires the use of different enzymes depending on the structure of the target, which makes it practically impossible to develop a general methodology.

The production of some oligosaccharides having lactose, galactose or GlcNAc at the reducing terminus, and optionally their allyl glycosides, has been reported by using genetically modified E. coli cells which have been able to internalize lactose, allyl galactoside, allyl lactoside or GlcNAc-OAll added as exogenous precursors to the fermentation broth (WO 01/04341, Fort et al. J. Chem. Soc., Chem. Comm. 2558 (2005), WO 2007/101862, EP-A-1911850, WO 2010/070104, US 2012/208181).

SUMMARY OF THE INVENTION

The invention relates to a method for producing a glycoconjugate comprising an oligosaccharide part covalently linked to a non-sugar moiety selected from the group consisting of amino acids, peptides, proteins, lipids, longer alkyl groups, polyethylene glycols, $\alpha,\beta$-unsaturated amido group and polyvinyl alcohols, the method comprising:

(i) providing a genetically modified cell comprising a gene encoding a glycosyl transferase enzyme that is able to transfer the glycosyl residue of an activated sugar nucleotide to an acceptor molecule intracellularly, (ii) culturing said genetically modified cell in the presence of an exogenous acceptor comprising a mono- or disaccharide part covalently linked to a non-sugar moiety selected from the group consisting of amino acids, peptides, proteins, lipids, longer alkyl groups, polyethylene glycols, $\alpha,\beta$-unsaturated amido group and polyvinyl alcohols, so that (a) said exogenous acceptor molecule is internalized by said genetically modified cell, and (b) said glycoconjugate is formed from said internalized acceptor molecule by a glycosyl transfer mediated by said glycosyl transferase enzyme expressed by said cell, and then (iii) separating said glycoconjugate from the culture medium.

Preferably, the mono- or disaccharide part of said exogenous acceptor is selected from galactose, glucose, N-acetylglucosamine and lactose, preferably lactose.

Also preferably, the recombinant glycosyl transferase enzyme is selected from the group consisting of N-acetylglucosaminyl transferases, galactosyl transferases, N-acetylgalactosaminyl transferases, glucuronosyl transferases, sialyl transferases and fucosyl transferases, more preferably $\beta$-1,3-N-acetyl-glucosaminyl transferase, $\beta$-1,6-N-acetyl-glucosaminyl transferase, $\beta$-1,3-galactosyl transferase, $\beta$-1,4-galactosyl transferase, $\beta$-1,3-N-acetyl-galactosaminyl transferase, $\beta$-1,3-glucuronosyl transferase, $\alpha$-2,3-sialyl transferase, $\alpha$-2,6-sialyl transferase, $\alpha$-2,8-sialyl transferase, $\alpha$-1,2-fucosyl transferase, $\alpha$-1,3-fucosyl transferase and $\alpha$-1,4-fucosyl transferase.

Particularly, in the method of the invention the genetically modified cell is E. coli of $LacZ^-$, $LacY^+$ genotype, the exogenous acceptor consists of lactose covalently linked to a non-sugar moiety selected from the group consisting of amino acids, peptides, proteins, lipids, longer alkyl groups, polyethylene glycols, $\alpha,\beta$-unsaturated amido group and polyvinyl alcohols, the glycosyl transferase is a fucosyl transferase, and the glycoconjugate produced by the method is a fucosylated lactose covalently linked to a non-sugar moiety selected from the group consisting of amino acids, peptides, proteins, lipids, longer alkyl groups, polyethylene glycols, $\alpha,\beta$-unsaturated amido group and polyvinyl alcohols, preferably the fucosylated lactose moiety is selected from 2'-fucosyllactose, 3-fucosyllactose and difucosyllactose.

Also particularly, in the method of the invention the genetically modified cell is *E. coli* of LacZ⁻, LacY⁺ genotype, the exogenous acceptor consists of lactose covalently linked to a non-sugar moiety selected from the group consisting of amino acids, peptides, proteins, lipids, longer alkyl groups, polyethylene glycols, α,β-unsaturated amido group and polyvinyl alcohols, the glycosyl transferase is a sialyl transferase, and the glycoconjugate produced by the method is a sialylated lactose covalently linked to a non-sugar moiety selected from the group consisting of amino acids, peptides, proteins, lipids, longer alkyl groups, polyethylene glycols, α,β-unsaturated amido group and polyvinyl alcohols, preferably the sialylated lactose moiety is selected from 3'-sialyllactose and 6'-sialyllactose.

Yet particularly, in the method of the invention the genetically modified cell is *E. coli* of LacZ⁻, LacY⁺ genotype, the exogenous acceptor consists of lactose covalently linked to a non-sugar moiety selected from the group consisting of amino acids, peptides, proteins, lipids, longer alkyl groups, polyethylene glycols, α,β-unsaturated amido group and polyvinyl alcohols, the glycosyl transferase is a sialyl transferase and a fucosyl transferase, and the glycoconjugate produced by the method is a sialylated and fucosylated lactose covalently linked to a non-sugar moiety selected from the group consisting of amino acids, peptides, proteins, lipids, longer alkyl groups, polyethylene glycols, α,β-unsaturated amido group and polyvinyl alcohols, preferably the sialylated fucosylated lactose moiety is 3'-sialyl-3-fucosyllactose.

Yet particularly, in the method of the invention the genetically modified cell is *E. coli* of LacZ⁻, LacY⁺ genotype, the exogenous acceptor consists of lactose covalently linked to a non-sugar moiety selected from the group consisting of amino acids, peptides, proteins, lipids, longer alkyl groups, polyethylene glycols, α,β-unsaturated amido group and polyvinyl alcohols, the glycosyl transferase is a N-acetylglucosaminyl transferase and optionally a galactosyl transferase, and the glycoconjugate produced by the method is a N-acetylglucosaminylated lactose optionally substituted by galactosyl residue and covalently linked to a non-sugar moiety selected from the group consisting of amino acids, peptides, proteins, lipids, longer alkyl groups, polyethylene glycols, α,β-unsaturated amido group and polyvinyl alcohols, preferably the N-acetylglucosaminylated lactose moiety optionally substituted by galactosyl residue is 3'-N-acetylglucosaminyl lactose, LNT or LNnT.

The second aspect of the invention is to provide a glycoconjugate consisting of an oligosaccharide, preferably a human milk oligosaccharide, attached to an amino acid, preferably serine, threonine or hydroxyproline, more preferably via an O-glycosidic linkage.

The third aspect of the invention relates to providing a glycoconjugate consisting of an oligosaccharide, preferably a human milk oligosaccharide, attached to a polyethylene glycol moiety via an O-glycosidic linkage.

DETAILED DESCRIPTION OF THE INVENTION

In accordance with this invention, an "oligosaccharide part or residue of a glycoconjugate" preferably means an oligosaccharide residue having at least two monosaccharide units. The oligosaccharide residue can have a linear or branched structure containing monosaccharide units that are linked to each other by interglycosidic linkages. The monosaccharides units can be any 5-9 carbon atom sugars that are aldoses (e.g. D-glucose, D-galactose, D-mannose, D-ribose, D-arabinose, L-arabinose, D-xylose, etc.), ketoses (e.g. D-fructose, D-sorbose, D-tagatose, etc.), deoxysugars (e.g. L-rhamnose, L-fucose, etc.), deoxy-aminosugars (e.g. N-acetylglucosamine, N-acetylmannosamine, N-acetylgalactosamine, etc.), uronic acids, ketoaldonic acids (e.g. sialic acid) or equivalents. The glycoconjugate has an oligosaccharide part covalently attached to a non-sugar moiety (aglycon) by either a covalent bond, which is a linkage between any atom of the oligosaccharide residue and any atom of the non-sugar moiety, or by a linker, which consists of one, two, three or four atoms such as —O—, —C—, —NH—, —N(OH)—, —S—, —C(=O)—, —C(=S)—, —C(=NH)—, —C(=N—OH)—, —C(=O)—O—, —O—C(=O)—, —C(=O)—S—, —S—C(=O)—, —C(=S)—O—, —O—C(=S)—, —C(=S)—S—, —S—C(=S)—, —C(=O)—NH—, —NH—C(=O)—, —C(=NH)—O—, —O—C(=NH)—, —C(=S)—NH—, —NH—C(=S)—, —C(=NH)—S— and —S—C(=NH). Preferably, the C-1 (in case of aldoses) or C-2 (in the case of ketoses) anomeric carbon atom of the reducing end of the oligosaccharide residue is linked to the non-sugar moiety by a covalent bond or a linker, thus forming O-, N-, S- or C-glycosides. Similarly, an "exogenous acceptor having a mono- or disaccharide part covalently attached to a non-sugar moiety" means that the mono- or disaccharide moiety is linked to the non-sugar moiety (aglycon) by either a covalent bond or by a linker in the above defined manner. The monosaccharide residue or the monosaccharide units of the disaccharide moiety can be those defined above.

Also in this invention, a "glycoconjugate having an oligosaccharide part covalently attached to an amino acid" preferably means an oligosaccharide as defined above that is linked to an amino acid by a covalent bond as defined above. The amino acid can be any natural or non-natural amino acid, that is an alkanoic acid derivative having at least one amino group as a substituent. Preferably, the amino acid is selected from the group consisting of α-amino acids and β-amino acids such as Ala, Arg, Asn, Asp, Cys, Glu, Gln, Gly, His, Ile, Leu, Lys, Met, Phe, Pro, Ser, Thr, Trp, Tyr, Val, hydroxyproline, α-methylserine, β-alanine, etc. The above-mentioned amino acids can be either directly bound to the carbohydrate or a mono- or disaccharide part, or via a linker defined above (e.g. for urea-linked glycopeptides see WO 2009/040363). Also preferably, the C-1 (in case of aldoses) or C-2 (in the case of ketoses) anomeric carbon atom of the reducing end of the carbohydrate or a mono- or disaccharide part is linked to the amino acid thus forming O-, N-, S- or C-glycosides. O-Glycosides (O-glycans) can be formed involving OH-containing amino acids such as serine, threonine, hydroxyproline, etc., N-glycosides (N-glycans) can be made using the α-, β-, etc. amino group of any amino acid or the additional amino group of the side chain of e.g. lysine, asparagine or glutamine, while C-glycosides (C-glycans) contain a C—C bond coupling a C-atom of the amino acid to a C-atom of the oligosaccharide part, preferably to the anomeric carbon atom of the non-reducing end. Correspondingly, an "exogenous acceptor having a mono- or disaccharide part covalently attached to an amino acid" means a mono- or disaccharide defined above that is linked to an amino acid by a covalent bond as defined above.

Herein, a "glycoconjugate having an oligosaccharide part covalently attached to a peptide" or an "exogenous acceptor having a mono- or disaccharide part covalently attached to a peptide" preferably means an oligosaccharide or a monoor disaccharide, respectively, defined above that is linked to an amino acid defined above by a covalent bond, provided that the amino acid is the part of an oligopeptide (also referred to as glycopeptides). The type of linkages can be similar to those mentioned above.

Also herein, a "glycoconjugate having an oligosaccharide part covalently attached to a protein" or an "exogenous acceptor having a mono- or disaccharide part covalently attached to a protein" preferably means a glycopeptide-like derivative wherein the amino acid attached to the carbohydrate moiety is a monomer unit of a protein; these compounds can be referred to as glycoproteins.

Also herein, a "glycoconjugate having an oligosaccharide part covalently attached to a lipid" preferably means an oligosaccharide defined above that is linked to a lipid by a covalent bond as defined above (also referred to as saccharolipids or glycolipids). "Lipid" denotes any organic compound, including fats, waxes, oils, sterols, fat-soluble vitamins (such as vitamins A, D, E and K), mono-, di- and triglycerides, sphingolipids and others, that are hydrophobic but soluble in alcohols, ether and most of other organic solvents; together with carbohydrates and protein they constitute basic and principal structural building blocks of living cells. Fatty acids are made of hydrocarbon chain having typically 4 to 28 carbon atoms, but preferably an even number of carbon atoms with a carboxyl group at the terminus (alkanoic acids), which carbon chain can be saturated or unsaturated one or more times and can be substituted by groups containing oxygen, halogen, nitrogen and/or sulfur. The double bond(s), if present, can be both cis or trans. Exemplary saturated fatty acids are caprylic acid, capric acid, lauric acid, myristic acid, palmitic acid, stearic acid, arachidic acid, behenic acid, lignoceric acid, cerotic acid, etc., and exemplary unsaturated fatty acids are miristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, etc. Fats and oils are mostly mixture of fatty acids and/or their esters with glycerol, whereas waxes are generally esters of fatty acids with long chain alcohols. Mono-, di- and triglycerides are mono-, di- and triesters of fatty acids, respectively, with glycerol. Sphingolipids are lipid-like compounds containing a sphingoid long-chain hydroxyl amine base (e.g. sphingosine) that is coupled to a fatty acid molecule through an amide bond, thereby forming the ceramide unit. All of these lipids can be attached to a saccharidic moiety, especially via the anomeric carbon atom of the non-reducing end of the saccharidic moiety. The most important glycolipids are glyceroglycolipids, glycosphingolipids (including cerebrosides, gangliosides, globosides and glycophosphosphingolipids) and lipopolysaccharides. Likewise, an "exogenous acceptor having a mono- or disaccharide part covalently attached to a lipid" means a mono- or disaccharide as defined above that is linked to a lipid by a covalent bond as defined above.

Also in this invention, a "glycoconjugate having an oligosaccharide part covalently attached to a polyethylene glycol" preferably means an oligosaccharide as defined above that is linked to the polyethylene glycol by a covalent bond as defined above. The polyethylene glycol (PEG) is a water soluble polyether of molecular formula $C_{2n}H_{4n+2}O_{n+1}$, having oxyethylene ($-CH_2-O-CH_2-$ or $CH_2-CH_2-O-$) repeating units and wherein n is 2 to 100, preferably 2 to 50, particularly 2 to 25, more particularly 2 to 10. Lower molecular weight PEGs are available in a purified form and are referred to as a "monodisperse PEG", and are also available as mixtures of PEGs and are referred to as a "polydisperse PEG". With regard to their geometry, PEGs can be in a linear, branched, star or comb configuration. Linear PEGs are preferably lower molecular weight PEGs (i.e., n is 2 to 10, preferably 3 to 6). Branched PEGs preferably have 3 to 10 linear, preferably lower molecular weight, PEG chains emanating from a central core group. Star PEGs preferably have 10 to 100 linear or branched, preferably lower molecular weight, PEG chains emanating from a central core group. Comb PEGs have multiple linear, branched and/or star, preferably lower molecular weight, PEG chains bonded to a polymer backbone. Terminal primary hydroxy group of PEGs can be bonded by an ether bond with an alkyl group, preferably methyl. In addition, their terminal hydroxy group can be replaced by amino, alkyl amino, dialkyl amino, acylamino, thiol or alkyl thio groups or their terminal hydroxymethyl group can be oxidized to a carboxyl, which can be esterified or be present in amide form with ammonia or a primary or secondary amine. PEGs can be attached to a saccharide unit at another one of its terminal ends. The attachment is preferably a glycosidic-like bond. Similarly, an "exogenous acceptor having a mono- or disaccharide part covalently attached to a PEG" means a mono- or disaccharide as defined above that is linked to a PEG by a covalent bond as defined above. Preferred PEGs are linear and of 2-10 repeating units.

Also herein, a "glycoconjugate having an oligosaccharide part covalently attached to polyvinyl alcohol" preferably means an oligosaccharide as defined above that is linked to a polyvinyl alcohol residue by a covalent bond as defined above. Polyvinyl alcohol (PVA) is a water-soluble polymer of molecular formula $(C_2H_4O)_x$ having $-CH_2-CH(OH)-$ monomer units. When attached to carbohydrate, either ends of the polymer chain can be glycosylated. Similarly, an "exogenous acceptor having a mono- or disaccharide part covalently attached to PVA" means a mono- or disaccharide as defined above that is linked to PVA by a covalent bond as defined above.

Also herein, a "longer alkyl chain" preferably means a linear or branched hydrocarbon chain having at least 6 carbon atoms, preferably 6-24 carbon atoms, that can be saturated or non-saturated. A "glycoconjugate having an oligosaccharide part covalently attached to a longer alkyl chain" or an "exogenous acceptor having a mono- or disaccharide part covalently attached to a longer alkyl chain" means that an above-defined hydrocarbon moiety is linked to an oligosaccharide defined above or a mono- or disaccharide defined above, respectively, by a covalent bond, preferably to the anomeric carbon atom of the carbohydrate in the form of an O-, N- or S-glycoside.

Also herein, an "α,β-unsaturated amido" preferably means a residue of formula A

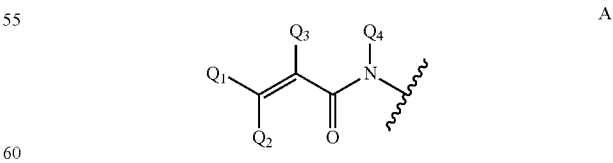

wherein $Q_1$, $Q_2$, $Q_3$ and $Q_4$ are, independently, H and $C_1$-$C_6$-alkyl, which alkyl optionally can be substituted with halogen, OH, nitro or phenyl groups. A "glycoconjugate having an oligosaccharide part covalently attached to an α,β-unsaturated amido group" or an "exogenous acceptor having a mono- or disaccharide part covalently attached to an α,β-unsaturated amido group" means that an above-defined residue of formula A, via its N atom, is linked to an oligosaccharide defined above or a mono- or disaccharide defined above, respectively, by a covalent bond, preferably to the anomeric carbon atom of the carbohydrate in the form of an N-glycoside.

Also herein, an "α,β-unsaturated carbonyl group" preferably means a residue of formula B

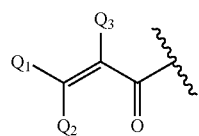

wherein $Q_1$, $Q_2$ and $Q_3$ are as defined at residue of formula A.

Preferably, in the above defined glycoconjugates and mono- or disaccharide derivatives the non-sugar (or non-carbohydrate) moiety is directly attached to the anomeric carbon atom.

Also herein, the term "human milk oligosaccharides" means tri- and higher oligosaccharides found in human milk (see Urashima et al.: *Milk oligosaccharides* Nova Medical Books, NY, 2011).

Also herein, a "genetically modified cell" preferably means a microorganism in which at least one alteration in its DNA sequence has been introduced into its genome in order that it has a particular phenotype. The alteration can result in a change in the original characteristics of the wild type cell, e.g., the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

In accordance with this invention, it has been surprisingly discovered that mono- and disaccharide conjugates, namely mono- and disaccharides covalently attached to a non-sugar moiety, which non-sugar moiety is selected from the group consisting of amino acids, peptides, proteins, lipids, longer alkyl groups, polyethylene glycols, α,β-unsaturated amido group and polyvinyl alcohols, preferably mono- and disaccharide conjugates containing a galactose residue, more preferably lactose conjugates can be internalized by a transport mechanism involving permeases, allowing thus this carbohydrate precursors to be glycosylated in a genetically modified cell able to act so.

Also in accordance with this invention, a glycoconjugate having an oligosaccharide part covalently linked to a non-sugar moiety, which is selected from the group consisting of amino acids, peptides, proteins, lipids, longer alkyl groups, polyethylene glycols, α,β-unsaturated amido group and polyvinyl alcohols, can be produced using a genetically modified cell, the method comprises:

(i) providing a genetically modified cell comprising one or more recombinant genes encoding one or more glycosyl transferase enzymes that are able to transfer the glycosyl residue of activated glycosyl nucleotides to an internalized acceptor molecule, (ii) culturing the genetically modified cell in the presence of an exogenous acceptor having a mono- or disaccharide part covalently attached to a non-sugar moiety, which non-sugar moiety is selected from the group consisting of amino acids, peptides, proteins, lipids, longer alkyl groups, polyethylene glycols, α,β-unsaturated amido group and polyvinyl alcohols, inducing (a) internalization of the exogenous acceptor molecule by the genetically modified cell, and (b) formation of the glycoconjugate of interest from the internalized acceptor molecule or glycosylated derivative thereof by one or more glycosyl transfers mediated by the one or more glycosyl transferase enzymes, and (iii) collecting the glycoconjugate from the fermentation broth.

The genetically modified cell used in the method according to the present invention can be selected from the group of bacteria and yeasts, preferably the genetically modified cell stems from a bacterium. Bacteria suitable for genetic modification preferably are selected from the group comprising *Escherichia coli*, *Bacillus* spp. (e.g. *Bacillus subtilis*), *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Neisseria gonorrhoeae*, *Neisseria meningitis*, *Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, among which *E. coli* is of preferable choice. The genetically modified cell used in connection to the present invention preferably lacks of enzyme activity directed to degrade the acceptor molecule, glycosylated derivative thereof and the glycoconjugate of interest as product of the method.

The genetically modified cell used in the method according to the present invention comprises one or more endogenous or recombinant genes encoding one or more glycosyl transferase enzymes that are able to transfer the glycosyl residue of an activated sugar nucleotide to an internalized acceptor molecule. The gene or an equivalent DNA sequence thereof, if it is recombinant, is introduced into the cell by known techniques, using an expression vector. The origin of the heterologous nucleic acid sequence can be any animal (including human) or plant, eukaryotic cells such as those from *Saccharomyces cerevisae*, *Saccharomyces pombe*, *Candida albicans* and the like, prokaryotic cells such as those originated from *E. coli*, *Bacillus subtilis*, *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Rhizobium meliloti*, *Neisseria gonorrhoeae* and *Neisseria meningitis*, or virus. The glycosyl transferase enzyme/enzymes expressed by the protein(s) encoded by the gene(s) or equivalent DNA sequence(s) are preferably glucosyl transferases, galactosyl transferases, N-acetylglucosaminyl transferases, N-acetylgalactosaminyl transferases, glucuronosyl transferases, xylosyl transferases, mannosyl transferases, fucosyl transferases, sialyl transferases and the like. In a preferred embodiment, the glycosyl transferases are selected from the group consisting of β-1,3-N-acetylglucosaminyl-transferase, β-1,6-N-acetylglucosaminyl-transferase, β-1,3-galactosyl-transferase, β-1,4-galactosyl-transferase, β-1,3-N-acetylgalactosaminyl-transferase, glucuronosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase. More preferably, the glycosyl transferases are selected from β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase. that is from those involved in the construction of HMO core structures as well as fucosylated and/or sialylated HMOs that are linked to a non-sugar moiety, which non-sugar moiety is selected from the group consisting of amino acids, peptides, proteins, lipids, longer alkyl groups, polyethylene glycols, α,β-unsaturated amido group and polyvinyl alcohols. The genes encoding the above-mentioned transferases have been described in the literature.

In glycosyl transferase mediated glycosylation reactions activated sugar nucleotides serve as donors. The activated sugar nucleotides generally comprising a phosphorylated glycosyl residue attached to a nucleoside, the specific glycosyl transferase enzyme accept only the specific sugar nucleotide. Thus, preferably the following activated sugar nucleotides are involved in the glycosyl transfer: UDP-Glc, UDP-Gal, UDP-GlcNAc, UDP-GalNAc, UDP-glucuronic acid, UDP-Xyl, GDP-Man, GDP-Fuc and CMP-sialic acid, particularly those selected from the group consisting of UDP-Gal, UDP-GlcNAc, GDP-Fuc and CMP-sialic acid.

In one embodiment of the method, the genetically modified cell used in the method according to the present invention has one or more sets of genes encoding one or more enzymes responsible for the synthesis of one or more activated glycosyl nucleotide mentioned above by a de novo pathway. The sets of genes are either naturally present in the cell or introduced into the cell by means of gene technology or recombinant DNA techniques, all of them are parts of the general knowledge of the skilled person. Also in this embodiment, the genetically modified cell having one or more sets of genes encoding one or more enzymes responsible for the synthesis of one or more activated glycosyl nucleotide by a de novo pathway produces one or more activated glycosyl nucleotide, ready for glycosylation in glycosyl transferase mediated reaction in the cell, when cultured. The production of the activated glycosyl nucleotides by the cell takes place under the action of enzymes involved in the de novo biosynthetic pathway of that respective sugar nucleotide stepwise reaction sequence starting from a simple carbon source like glycerol, fructose or glucose (for a review for monosaccharide metabolism see e.g. H. H. Freeze and A. D. Elbein: *Chapter 4: Glycosylation precursors*, in: Essentials of Glycobiology, $2^{nd}$ edition (Eds. A. Varki et al.), Cold Spring Harbour Laboratory Press (2009)).

According to the preferred embodiment disclosed above, the genetically modified cell is cultured in the presence of a carbon-based substrate such as glycerol, glucose, glycogen, fructose, maltose, starch, cellulose, pectin, chitin, etc. Preferably, the cell culturing is performed on glycerol and/or glucose and/or fructose.

In another embodiment, the genetically modified cell can utilize salvaged monosaccharide for producing activated sugar nucleotide. In the salvage pathway, monosaccharides derived from degraded oligosaccharides phosphorylated by kinases, and converted to nucleotide sugars by pyrophosphorylases. The enzymes involved in the procedure can be heterologous ones, or native ones of the cell used for genetic modification. Preferably, the synthesis of UDP-arabinose, GDP-fucose or CMP-sialic acid can be accomplished using the salvage pathway when exogenous arabinose, fucose or sialic acid is also added to the culture.

It should be emphasized, that whatever way, either the de novo, or the salvage pathway taken for producing activated sugar nucleotides by the genetically modified cell is advantageous compared to in vitro versions of transfer glycosylation, as it avoids using the very expensive sugar nucleotide type donors added exogenously, hence the donors are formed by the cell in situ and the phosphatidyl nucleoside leaving groups are recycled in the cell.

The method of this invention is also based on the way transporting an exogenous acceptor molecule into the genetically modified cell for glycosylation thus producing glycoconjugates of interest. The internalization cannot affect the basic and vital functions or destroy the integrity of the cell. In one embodiment the internalization takes place via a passive transport mechanism during which the exogenous acceptor molecule diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards an equilibrium. In other embodiment the exogenous precursor is internalized with the aid of an active transport. In this case the genetically modified cell used in the method claimed comprises transporter proteins, called permeases, with which the cell is able to admit exogenous substances and to concentrate them in the cytoplasm. Permeases act as enzymes, mention should be made of lactose permease (LacY) and sucrose permease (CscB). LacY has specificity towards galactose and simple galactosyl disaccharides, CscB is supposed to transport fructose and fructosyl disaccharides (see e.g. J. Sugihara et al. *Biochem.* 50, 11009 (2011)). The specificity towards the sugar moiety of the substrate to be internalized can be altered by mutation by means of known recombinant DNA techniques. In a preferred embodiment the internalization of the exogenous lactose derivative acceptor takes place via an active transport mechanism mediated by lactose permease.

During fermentation the exogenous substrate is internalized to and accumulated in the cell. The internalized substrate, acting as acceptor, participates in a glycosyl transferase induced glycosylation reaction, in which a glycosyl residue of an activated nucleotide donor is transferred so that the acceptor is glycosylated. Optionally, when more than one glycosyl transferase is expressed by the cell, additional glycosylation reactions can occur resulting in the formation of the target glycoconjugate. Thus the expression "formation of the glycoconjugate of interest from the glycosylated derivative of the internalized acceptor molecule" in describing the method to be claimed refers to the case when at least two, identical or different monosaccharide units are transferred to the acceptor added exogenously and internalized by an active and/or passive mechanism by the cell, and the so glycosylated acceptor derivative is not yet intended to be the target glycoconjugate of interest, instead it is involved in further glycosylation reaction(s) in order to make the glycoconjugate of interest to be isolated. Of course, the cell preferably lacks any enzyme activity which would degrade the acceptor or the oligosaccharide derivatives produced in the cell.

At the end of incubation the glycoconjugate of interest as product of the method can be accumulated both in the intra- and the extracellular matrix. The product can be transported to the supernatant in a passive way, that is it diffuses outside across the cell membrane. The transport can be facilitated by sugar efflux transporters, proteins that promote the effluence of sugar derivatives from the cell to the supernatant. The sugar efflux transporter can be present exogenously or endogenously and is overexpressed under the conditions of the fermentation to enhance the export of the oligosaccharide derivative produced. The specificity towards the sugar moiety of the product to be secreted can be altered by mutation by means of known recombinant DNA techniques.

According to a preferred embodiment, the method also comprises the addition of an inducer to the culture medium. The role of the inducer is to promote the expression of enzymes involved in the de novo or salvage pathway and/or of permeases involved in the active transport and/or of sugar efflux transporters of the cell. Preferably, the inducer is isopropyl-β-D-thiogalactoside (IPTG).

In step (iii) of the method according to the present invention the glycoconjugate of interest is collected from the fermentation broth. According to a general manipulation, the supernatant containing the glycoconjugate of interest is separated from the cells by centrifugation. The separated cells are resuspended in water and subjected to heat and/or acid treatment in order to be permeabilized for releasing the glycoconjugates of interest piled up intracellularly. The product is separated from the treated cell by centrifugation. The two supernatants containing the extra- and intracellular products, respectively, are combined and the products are purified and isolated by means of standard separation, purification and isolation techniques like gel and/or cationic ion exchange resin ($H^+$ form) chromatography. Preferably, the oligosaccharide derivative is collected only from the supernatant.

When carrying out a fermentation, a genetically modified cell, particularly a Lac $Z^-Y^+$ E. coli cell, is preferably cultured in the following way:

(a) a first phase of exponential cell growth ensured by a carbon-based substrate, and (b) a second phase of cell growth limited by a carbon-based substrate which is added continuously.

Preferably, said carbon-based substrate is selected from the group consisting of glycerol and glucose. More preferably, the carbon-based substrate added during the second phase glycerol.

Also preferably, said culturing is performed under conditions allowing the production of a culture with a high cell density.

Also preferably, said culturing further comprises a third phase of slowed cell growth obtained by continuously adding to the culture an amount of said carbon-based substrate that is less than the amount of the carbon-based substrate added in said second phase so as to increase the content of the product produced in the high cell density culture.

Also preferably, the amount of the carbon-based substrate added continuously to the cell culture during said third phase is at least 30% less than the amount of the carbon-based substrate added continuously during said second phase.

Also preferably, the method further comprises the addition of an inducer to said culture medium to induce the expression in said cell of said enzyme and/or of a protein involved in said transport. The inducer is preferably isopropyl β-D-thiogalactoside (IPTG) and the protein is lactose permease.

The exogenous acceptor having a mono- or disaccharide part covalently attached to a non-sugar moiety, which non-sugar moiety is selected from the group consisting of amino acids, peptides, proteins, lipids, longer alkyl groups, polyethylene glycols, α,β-unsaturated amido group and polyvinyl alcohols, to be internalized by and glycosylated in the fermented cell can be added to the culture medium at once or continuously. If added, it is done. The pure acceptor as solid/liquid or a concentrated aqueous solution of the acceptor can be added at once at the end of the first phase of exponential cell growth, then the fermentation is continued by addition of the carbon-based substrate as described above. Alternatively, the continuous addition is beneficial when higher amount exogenous acceptor is intended to be used at a given volume. To avoid overflow metabolism and other side processes during the fermentation, the exogenous acceptor is dissolved in the feeding solution to be added during the second (and optionally the third) phase, therefore a continuous addition of the acceptor (with the carbon-based substrate) is realized.

According to a first particular embodiment, it is provided a method for producing a glycoconjugate of interest having an oligosaccharide part covalently linked to an amino acid using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to an amino acid inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The amino acid moiety is preferably selected from serine, threonine and hydroxyproline, more preferably serine.

The genetically modified cell can have more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a mono- or disaccharide covalently linked, as defined above, to an amino acid, preferably serine, threonine or hydroxyproline, more preferably serine, and the glycoconjugate of interest is an oligosaccharide covalently linked, as defined above, to an amino acid, preferably serine, threonine or hydroxyproline, more preferably serine, and they form an O-glycoside.

Also preferably with regard to the first particular embodiment, the method comprises:

(i) providing a genetically modified cell comprising
a gene, preferably a recombinant gene encoding a glycosyl transferase enzyme that is able to transfer the glycosyl residue of an activated sugar nucleotide to an internalized acceptor molecule, and
a set of genes encoding enzymes responsible for the synthesis of the activated sugar nucleotide by a de novo pathway, (ii) culturing the genetically modified cell in the presence of an exogenous acceptor, which is selected from serine, threonine and hydroxyproline O-glycosides of a mono- or disaccharide, particularly a serine O-glycoside of a mono- or disaccharide, inducing (a) internalization of said exogenous acceptor molecule via an active and/or passive transport mechanism by the genetically modified cell, (b) formation of the activated sugar nucleotide by a de novo pathway, and (c) formation of a glycoconjugate selected from serine, threonine and hydroxyproline O-glycans, preferably a serine O-glycan, from said internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of said exogenous serine, threonine or hydroxyproline O-glycoside acceptor is selected from galactose, glucose, N-acetyl-glucosamine and lactose, more preferably lactose, particularly serine O-glycoside of lactose, the internalization of the above defined exogenous acceptor takes place via an active transport mechanism mediated by a permease, preferably a lactose permease, and the product of the fermentation is selected from a serine, threonine and hydroxyproline O-glycosides of glycosylated galactose, glucose, N-acetyl-glucosamine and lactose, more preferably of glycosylated lactose, particularly serine O-glycoside of glycosylated lactose.

According to an even more preferable way to perform this first particular embodiment of the present invention, the genetically modified cell is $E.\ coli$ of $LacZ^-$, $LacY^+$ genotype, the exogenous acceptor is serine, threonine or hydroxyproline, preferably serine, O-glycoside of lactose, the glycosyl transferase is at least one fucosyl-transferase and/or at least one sialyl-transferase and/or at least one N-acetylglucosaminyl-transferase and/or at least one galactosyl-transferase, and the glycoconjugate of interest produced by the method is a serine, threonine or hydroxyproline, preferably serine, O-glycoside of fucosylated and/or sialylated and/or N-acetylglucosaminylated and/or galactosylated lactose, preferably of a human milk oligosaccharide.

Accordingly, the method even more preferably comprises:

(i) providing a genetically modified $E.\ coli$ cell of $LacZ^-$, $LacY^+$ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified $E.\ coli$ cell of $LacZ^-$, $LacY^+$ genotype in the presence of an exogenous acceptor which is serine, threonine or hydroxyproline, preferably serine, O-glycoside of lactose, inducing (a) internalization of the exogenous serine, threonine or hydroxyproline, preferably serine, O-glycoside of lactose via an active transport mechanism by a lactose permease of the genetically modified cell, (b) formation of an activated fucose nucleotide, preferably GDP-fucose, by a de novo pathway, and formation of a glycoconjugate from the internalized serine, threonine or hydroxyproline, preferably serine, O-glycoside of lactose by a fucosyl transfer mediated by the fucosyl transferase enzyme, (iii) collecting the glycoconjugate that is a fucosylated serine, threonine or hydroxyproline, preferably serine, O-glycoside of lactose, preferably serine, threonine or hydroxyproline, preferably serine, O-glycoside of 2'-fucosyllactose, 3-fucosyllactose or difucosyllactose, from the culture medium.

Yet even more preferably, the method comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified $E.\ coli$ cell of $LacZ^-$, $LacY^+$ genotype in the presence of an exogenous acceptor that is serine, threonine or hydroxyproline, preferably serine, O-glycoside of lactose, inducing (a) internalization of the exogenous serine, threonine or hydroxyproline, preferably serine, O-glycoside of lactose via an active transport mechanism by a lactose permease of the genetically modified cell, (b) formation of an activated sialic acid nucleotide, preferably CMP-sialic acid, by a de novo pathway, and (c) formation of a glycoconjugate from the internalized serine, threonine or hydroxyproline, preferably serine, O-glycoside of lactose by a sialyl transfer mediated by the sialyl transferase enzyme, (iii) collecting the glycoconjugate that is a sialylated serine, threonine or hydroxyproline, preferably serine, O-glycoside of lactose, preferably serine, threonine or hydroxyproline, preferably serine, O-glycoside of 3'-sialyllactose or 6'-sialyllactose, from the culture medium.

Yet even more preferably, the method comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of the activated fucose nucleotide, preferably GDP-fucose, by a de novo pathway, (ii) culturing the genetically modified $E.\ coli$ cell of $LacZ^-$, $LacY^+$ genotype in the presence of an exogenous acceptor that is serine, threonine or hydroxyproline, preferably serine, O-glycoside of lactose, inducing (a) internalization of the exogenous serine, threonine or hydroxyproline, preferably serine, O-glycoside of lactose via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized serine, threonine or hydroxyproline, preferably serine, O-glycoside of lactose by a sialyl transfer mediated by the sialyl transferase enzyme, and by a fucosyl transfer mediated by the fucosyl transferase enzyme, (iii) collecting the glycoconjugate that is a sialylated and fucosylated serine, threonine or hydroxyproline, preferably serine, O-glycoside of lactose, preferably serine, threonine or hydroxyproline, preferably serine, O-glycoside of 3'-sialyl-3-fucosyllactose, from the culture medium.

Yet even more preferably, the method comprises:

(i) providing a genetically modified $E.\ coli$ cell of $LacZ^-$, $LacY^+$ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and optionally a set of genes encoding enzymes responsible for the synthesis of the activated Gal nucleotide, preferably UDP-Gal, by a de novo pathway, (ii) culturing the genetically modified $E.\ coli$ cell of $LacZ^-$, $LacY^+$ genotype in the presence of an exogenous acceptor that is serine, threonine or hydroxyproline, preferably serine, O-glycoside of lactose, inducing (a) internalization of the exogenous serine, threonine or hydroxyproline, preferably serine, O-glycoside of lactose via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the glycoconjugate of interest from the internalized serine, threonine or hydroxyproline, preferably serine, O-glycoside of lactose by a N-acetylglucosaminyl transfer mediated by the N-acetylglucosaminyl transferase enzyme optionally followed by a galactosyl transfer mediated by the galactosyl transferase enzyme, (iii) collecting the glycoconjugate that is an N-acetylglucosaminylated serine, threonine or hydroxyproline, preferably serine, O-glycoside of lactose optionally substituted by galactose, preferably serine, threonine or hydroxyproline, preferably serine, O-glycoside of 3'-N-acetylglucosaminyl lactose, LNT or LNnT, from the culture medium.

The most preferred way to carry out the first particular embodiment of the invention comprises:

(i) providing a genetically modified $E.\ coli$ cell of $LacZ^-$, $LacY^+$ genotype comprising a recombinant gene encoding an α-1,2-fucosyl transferase, and a set of genes encoding enzymes responsible for the synthesis of GDP-fucose by a de novo pathway, (ii) culturing the genetically modified $E.\ coli$ cell of $LacZ^-$, $LacY^+$ genotype in the presence of an exogenous acceptor that is serine, threonine or hydroxyproline, preferably serine, O-glycoside of lactose, inducing (a) internalization of the exogenous serine, threonine or hydroxyproline, preferably serine, O-glycoside of lactose via an active transport mechanism by a lactose permease of the genetically modified cell, (b) formation of GDP-fucose by a de novo pathway, and (c) formation of a glycoconjugate from the internalized serine, threonine or hydroxyproline, preferably serine, O-glycoside of lactose by a fucosyl transfer mediated by the α-1,2-fucosyl transferase, (iii) collecting the glycoconjugate that is a serine, threonine or hydroxyproline, preferably serine, O-glycoside of 2'-fucosyllactose, from the culture medium.

According to a second particular embodiment, it is provided a method for producing a glycoconjugate of interest having an oligosaccharide part covalently linked to a peptide using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to a peptide inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor that is a mono- or disaccharide part covalently linked to a peptide as defined above, and the glycoconjugate of interest that is an oligosaccharide part covalently linked to a peptide as defined above.

Also preferably with regard to the second particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous acceptor that is a mono- or disaccharide part covalently linked to a peptide inducing (a) internalization of the exogenous acceptor molecule via an active and/or passive transport mechanism by the genetically modified cell, (b) formation of the activated sugar nucleotide by a de novo pathway, and (c) formation of the glycoconjugate from the internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous acceptor molecule is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is selected from a glycosylated galactose, glucose, N-acetyl-glucosamine and lactose covalently linked to a peptide, more preferably glycosylated lactose covalently linked to a peptide.

According to an even more preferable way performing this second particular embodiment of the present invention, the genetically modified cell is E. coli of LacZ⁻, LacY⁺ genotype, the exogenous acceptor is lactose covalently linked to a peptide, the glycosyl transferase is at least one fucosyl-transferase and/or at least one sialyl-transferase and/or at least one N-acetylglucosaminyl-transferase and/or at least one galactosyl-transferase, and the glycoconjugate of interest produced by the method is a fucosylated and/or sialylated and/or N-acetylglucosaminylated and/or galactosylated lactose, preferably a human milk oligosaccharide, covalently linked to a peptide.

Accordingly, the method most preferably comprises:
(i) providing a genetically modified E. coli cell of LacZ⁻, LacY⁺ genotype comprising
a gene, preferably a recombinant gene encoding a fucosyl transferase enzyme that is able to transfer the fucosyl residue of an activated fucose nucleotide to an internalized acceptor molecule, and
a set of genes encoding enzymes responsible for the synthesis of the activated fucose nucleotide, preferably GDP-fucose, by a de novo pathway,
(ii) culturing the genetically modified E. coli cell of LacZ⁻, LacY⁺ genotype in the presence of an exogenous acceptor that is lactose covalently linked to a peptide inducing
(a) internalization of the exogenous lactose acceptor derivative via an active transport mechanism by a lactose permease of the genetically modified cell,
(b) formation of an activated fucose nucleotide, preferably GDP-fucose, by a de novo pathway, and
(c) formation of a glycoconjugate from the internalized lactose acceptor derivative by a fucosyl transfer mediated by the fucosyl transferase enzyme,
(iii) collecting the glycoconjugate that is a fucosylated lactose, preferably 2'-fucosyllactose, 3-fucosyllactose or difucosyllactose, covalently linked to a peptide from the culture medium.

Moreover, the method most preferably comprises:
(i) providing a genetically modified E. coli cell of LacZ⁻, LacY⁺ genotype comprising
a gene, preferably a recombinant gene encoding a sialyl transferase enzyme that is able to transfer the sialyl residue of an activated sialic acid nucleotide to an internalized acceptor molecule, and
a set of genes encoding enzymes responsible for the synthesis of the activated sialic acid nucleotide, preferably CMP-sialic acid, by a de novo pathway,
(ii) culturing the genetically modified E. coli cell of LacZ⁻, LacY⁺ genotype in the presence of an exogenous acceptor that is lactose covalently linked to a peptide inducing
(a) internalization of the exogenous lactose acceptor derivative via an active transport mechanism by a lactose permease of the genetically modified cell,
(b) formation of an activated sialic acid nucleotide, preferably CMP-sialic acid, by a de novo pathway, and
(c) formation of a glycoconjugate from the internalized lactose acceptor derivative by a sialyl transfer mediated by the sialyl transferase enzyme,
(iii) collecting the glycoconjugate that is a sialylated lactose, preferably 3'-sialyllactose or 6'-sialyllactose, covalently linked to a peptide from the culture medium.

In addition, the method most preferably comprises:
(i) providing a genetically modified E. coli cell of LacZ⁻, LacY⁺ genotype comprising
a gene, preferably a recombinant gene encoding a sialyl transferase enzyme that is able to transfer the sialyl residue of an activated sialic acid nucleotide to an internalized acceptor molecule,
a gene, preferably a recombinant gene encoding a fucosyl transferase enzyme that is able to transfer the sialyl residue of an activated sialic acid nucleotide to an internalized acceptor molecule,
a set of genes encoding enzymes responsible for the synthesis of the activated sialic acid nucleotide, preferably CMP-sialic acid, by a de novo pathway, and
a set of genes encoding enzymes responsible for the synthesis of the activated fucose nucleotide, preferably GDP-fucose, by a de novo pathway,
(ii) culturing the genetically modified E. coli cell of LacZ⁻, LacY⁺ genotype in the presence of an exogenous acceptor that is lactose covalently linked to a peptide inducing
(a) internalization of the exogenous lactose acceptor derivative via an active transport mechanism by a lactose permease of the genetically modified cell,
(b) formation of an activated sialic acid nucleotide, preferably CMP-sialic acid, by a de novo pathway,
(c) formation of an activated fucose nucleotide, preferably GDP-fucose, by a de novo pathway, and
(d) formation of a glycoconjugate from the internalized lactose acceptor derivative by a sialyl transfer mediated by the sialyl transferase enzyme, and by a fucosyl transfer mediated by the fucosyl transferase enzyme,
(iii) collecting the glycoconjugate that is a sialylated fucosylated lactose, preferably 3'-sialyl-3-fucosyllactose, covalently linked to a peptide from the culture medium.

Furthermore, the method most preferably comprises:
(i) providing a genetically modified E. coli cell of LacZ⁻, LacY⁺ genotype comprising
a gene, preferably a recombinant gene encoding a N-acetylglucosaminyl transferase enzyme that is able to transfer the N-acetylglucosaminyl residue of an activated GlcNAc nucleotide to an internalized acceptor molecule,
optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and a set of genes encoding enzymes responsible for the synthesis of the activated Gal nucleotide, preferably UDP-Gal, by a de novo pathway, (ii) culturing the genetically modified *E. coli* cell of LacZ$^-$, LacY$^+$ genotype in the presence of an exogenous acceptor that is lactose covalently linked to a peptide inducing (a) internalization of the exogenous lactose derivative via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the glycoconjugate of interest from the internalized lactose derivative by a N-acetylglucosaminyl transfer mediated by the N-acetylglucosaminyl transferase enzyme optionally followed by a galactosyl transfers mediated by the galactosyl transferase enzyme, (iii) collecting the glycoconjugate that is an N-acetylglucosaminylated lactose optionally substituted by galactose and covalently linked to a peptide, preferably 3'-N-acetylglucosaminyl lactose, LNT or LNnT covalently linked to a peptide from the culture medium.

According to a third particular embodiment, it is provided a method for producing a glycoconjugate of interest having an oligosaccharide part covalently linked to a protein using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor comprising a mono- or disaccharide part covalently linked to a protein inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor that is a mono- or disaccharide part covalently linked to a protein as defined above, and the glycoconjugate of interest that is an oligosaccharide part covalently linked to a protein as defined above.

Also preferably with regard to the third particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous acceptor that is a mono- or disaccharide part covalently linked to a protein inducing (a) internalization of the exogenous acceptor molecule via an active and/or passive transport mechanism by the genetically modified cell, (b) formation of the activated sugar nucleotide by a de novo pathway, and (c) formation of the glycoconjugate from the internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of said exogenous acceptor molecule is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is selected from a glycosylated galactose, glucose, N-acetyl-glucosamine and lactose covalently linked to a protein, more preferably glycosylated lactose covalently linked to a protein.

According to an even more preferable way performing this third particular embodiment of the present invention, the genetically modified cell is *E. coli* of LacZ$^-$, LacY$^+$ genotype, the exogenous acceptor is lactose covalently linked to a protein, the glycosyl transferase is at least one fucosyl-transferase and/or at least one sialyl-transferase and/or at least one N-acetylglucosaminyl-transferase and/or at least one galactosyl-transferase, and the glycoconjugate of interest produced by the method is a fucosylated and/or sialylated and/or N-acetylglucosaminylated and/or galactosylated lactose, preferably a human milk oligosaccharide, covalently linked to a protein.

Accordingly, the method most preferably comprises:

(i) providing a genetically modified *E. coli* cell of LacZ$^-$, LacY$^+$ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified *E. coli* cell of LacZ⁻, LacY⁺ genotype in the presence of an exogenous acceptor that is lactose covalently linked to a protein inducing (a) internalization of the exogenous lactose acceptor derivative via an active transport mechanism by a lactose permease of the genetically modified cell, (b) formation of an activated fucose nucleotide, preferably GDP-fucose, by a de novo pathway, and (c) formation of a glycoconjugate from the internalized lactose acceptor derivative by a fucosyl transfer mediated by the fucosyl transferase enzyme, (iii) collecting the glycoconjugate that is a fucosylated lactose, preferably 2'-fucosyllactose, 3-fucosyllactose or difucosyllactose, covalently linked to a protein from the culture medium.

Moreover, the method most preferably comprises:

(i) providing a genetically modified *E. coli* cell of LacZ⁻, LacY⁺ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified *E. coli* cell of LacZ⁻, LacY⁺ genotype in the presence of an exogenous acceptor that is lactose covalently linked to a protein inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, and (c) formation of a glycoconjugate from the internalized lactose acceptor derivative by a sialyl transfer mediated by the sialyl transferase enzyme, (iii) collecting the glycoconjugate that is a sialylated lactose, preferably 3'-sialyllactose or 6'-sialyllactose, covalently linked to a protein from the culture medium.

In addition, the method most preferably comprises:

(i) providing a genetically modified *E. coli* cell of LacZ⁻, LacY⁺ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of said activated fucose nucleotide, preferably GDP-fucose, by a de novo pathway, (ii) culturing said genetically modified *E. coli* cell of LacZ⁻, LacY⁺ genotype in the presence of an exogenous acceptor that is lactose covalently linked to a protein inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized lactose acceptor derivative by a sialyl transfer mediated by the sialyl transferase enzyme, and by a fucosyl transfer mediated by the fucosyl transferase enzyme, (iii) collecting the glycoconjugate that is a sialylated fucosylated lactose, preferably 3'-sialyl-3-fucosyllactose, covalently linked to a protein from the culture medium.

Furthermore, the method most preferably comprises:

(i) providing a genetically modified *E. coli* cell of LacZ⁻, LacY⁺ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and a set of genes encoding enzymes responsible for the synthesis of the activated Gal nucleotide, preferably UDP-Gal, by a de novo pathway, (ii) culturing the genetically modified *E. coli* cell of LacZ⁻, LacY⁺ genotype in the presence of an exogenous acceptor that is lactose covalently linked to a protein inducing (a) internalization of the exogenous lactose derivative via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the glycoconjugate of interest from the internalized lactose derivative by a N-acetylglucosaminyl transfer mediated by the N-acetylglucosaminyl transferase enzyme optionally followed by a galactosyl transfers mediated by the galactosyl transferase enzyme, (iii) collecting the glycoconjugate that is an N-acetylglucosaminylated lactose optionally substituted by galactose and covalently linked to a protein, preferably 3'-N-acetylglucosaminyl lactose, LNT or LNnT covalently linked to a protein from the culture medium.

According to a fourth particular embodiment, it is provided a method for producing a glycoconjugate of interest having an oligosaccharide part covalently linked to a lipid using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor comprising a mono- or disaccharide part covalently linked to a lipid inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a mono- or disaccharide part covalently linked to a lipid as defined above, and the glycoconjugate of interest is an oligosaccharide part covalently linked to a lipid as defined above.

Also preferably with regard to the fourth particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous acceptor that is a mono- or disaccharide part covalently linked to a lipid inducing (a) internalization of the exogenous acceptor molecule via an active and/or passive transport mechanism by the genetically modified cell, (b) formation of the activated sugar nucleotide by a de novo pathway, and (c) formation of the glycoconjugate from the internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous acceptor molecule is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is selected from a glycosylated galactose, glucose, N-acetyl-glucosamine and lactose covalently linked to a lipid, more preferably glycosylated lactose covalently linked to a lipid.

According to an even more preferable way performing this fourth particular embodiment of the present invention, the genetically modified cell is $E.\ coli$ of $LacZ^-$, $LacY^+$ genotype, the exogenous acceptor is lactose covalently linked to a lipid, the glycosyl transferase is at least one fucosyl-transferase and/or at least one sialyl-transferase and/or at least one N-acetylglucosaminyl-transferase and/or at least one galactosyl-transferase, and the glycoconjugate of interest produced by the method is a fucosylated and/or sialylated and/or N-acetylglucosaminylated and/or galactosylated lactose, preferably a human milk oligosaccharide, covalently linked to a lipid.

Accordingly, the method most preferably comprises:

(i) providing a genetically modified $E.\ coli$ cell of $LacZ^-$, $LacY^+$ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified $E.\ coli$ cell of $LacZ^-$, $LacY^+$ genotype in the presence of an exogenous acceptor that is lactose covalently linked to a lipid inducing (a) internalization of the exogenous lactose acceptor derivative via an active transport mechanism by a lactose permease of the genetically modified cell, (b) formation of an activated fucose nucleotide, preferably GDP-fucose, by a de novo pathway, and (c) formation of a glycoconjugate from the internalized lactose acceptor derivative by a fucosyl transfer mediated by the fucosyl transferase enzyme, (iii) collecting the glycoconjugate that is a fucosylated lactose, preferably 2'-fucosyllactose, 3-fucosyllactose or difucosyllactose, covalently linked to a lipid from the culture medium.

Moreover, the method most preferably comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified $E.\ coli$ cell of $LacZ^-$, $LacY^+$ genotype in the presence of an exogenous acceptor that is lactose covalently linked to a lipid inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, and (c) formation of a glycoconjugate from the internalized lactose acceptor derivative by a sialyl transfer mediated by the sialyl transferase enzyme, (iii) collecting the glycoconjugate that is a sialylated lactose, preferably 3'-sialyllactose or 6'-sialyllactose, covalently linked to a lipid from the culture medium.

In addition, the method most preferably comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of the activated fucose nucleotide, preferably GDP-fucose, by a de novo pathway, (ii) culturing the genetically modified *E. coli* cell of LacZ⁻, LacY⁺ genotype in the presence of an exogenous acceptor that is lactose covalently linked to a lipid inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized lactose acceptor derivative by a sialyl transfer mediated by the sialyl transferase enzyme, and by a fucosyl transfer mediated by the fucosyl transferase enzyme, (iii) collecting the glycoconjugate that is a sialylated fucosylated lactose, preferably 3'-sialyl-3-fucosyllactose, covalently linked to a lipid from the culture medium.

Furthermore, the method most preferably comprises:

(i) providing a genetically modified *E. coli* cell of LacZ⁻, LacY⁺ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and a set of genes encoding enzymes responsible for the synthesis of the activated Gal nucleotide, preferably UDP-Gal, by a de novo pathway, (ii) culturing the genetically modified *E. coli* cell of LacZ⁻, LacY⁺ genotype in the presence of an exogenous acceptor that is lactose covalently linked to a lipid inducing (a) internalization of the exogenous lactose derivative via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the glycoconjugate of interest from the internalized lactose derivative by a N-acetylglucosaminyl transfer mediated by the N-acetylglucosaminyl transferase enzyme optionally followed by a galactosyl transfers mediated by the galactosyl transferase enzyme, (iii) collecting the glycoconjugate that is an N-acetylglucosaminylated lactose optionally substituted by galactose and covalently linked to a lipid, preferably 3'-N-acetylglucosaminyl lactose, LNT or LNnT covalently linked to a lipid from the culture medium.

According to a fifth particular embodiment, it is provided a method for producing a glycoconjugate of interest having an oligosaccharide part covalently linked to a longer alkyl group using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to a longer alkyl group inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The longer alkyl group preferably consists of 6-24 carbon atoms, is preferably linear and saturated, and forms with the carbohydrate part of the acceptor and the glycoconjugate, to which it is attached, an O-glycoside. More preferably, the longer alkyl group consists of 6-20, even more preferably 6-14, particularly 6-10 carbon atoms.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a $C_6$-$C_{20}$, preferably a $C_6$-$C_{14}$, more preferably a $C_6$-$C_{10}$-alkyl O-glycoside of a mono- or disaccharide, and the glycoconjugate produced is a $C_6$-$C_{20}$, preferably a $C_6$-$C_{14}$, more preferably a $C_6$-$C_{10}$-alkyl O-glycoside of an oligosaccharide.

Also preferably with regard to the fifth particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous $C_6$-$C_{20}$, preferably a $C_6$-$C_{14}$, more preferably a $C_6$-$C_{10}$-alkyl O-glycoside of a mono- or disaccharide, inducing (a) internalization of the exogenous $C_6$-$C_{20}$, preferably a $C_6$-$C_{14}$, more preferably a $C_6$-$C_{10}$-alkyl O-glycoside of a mono- or disaccharide via an active and/or passive transport mechanism by the genetically modified cell, (b) formation of the activated sugar nucleotide by a de novo pathway, and (c) formation of the $C_6$-$C_{20}$, preferably a $C_6$-$C_{14}$, more preferably a $C_6$-$C_{10}$-alkyl O-glycoside of a glycoconjugate from the internalized $C_6$-$C_{20}$, preferably a $C_6$-$C_{14}$, more preferably a $C_6$-$C_{10}$-alkyl O-glycoside of a mono- or disaccharide by a glycosyl transfers mediated by the glycosyl transferase enzyme, (iii) collecting the $C_6$-$C_{20}$, preferably a $C_6$-$C_{14}$, more preferably a $C_6$-$C_{10}$-alkyl O-glycoside of a glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous $C_6$-$C_{20}$, preferably a $C_6$-$C_{14}$, more preferably a $C_6$-$C_{10}$-alkyl O-glycoside acceptor is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is selected from a glycosylated $C_6$-$C_{20}$, preferably a $C_6$-$C_{14}$, more preferably a $C_6$-$C_{10}$-alkyl O-glycoside of galactose, glucose, N-acetyl-glucosamine and lactose, more preferably glycosylated $C_6$-$C_{20}$, preferably a $C_6$-$C_{14}$, more preferably a $C_6$-$C_{10}$-alkyl O-glycoside of lactose.

According to an even more preferable way to perform this fifth particular embodiment of the present invention, the genetically modified cell is *E. coli* of LacZ$^-$, LacY$^+$ genotype, the exogenous acceptor is $C_6$-$C_{20}$, preferably a $C_6$-$C_{14}$, more preferably a $C_6$-$C_{10}$-alkyl O-glycoside of lactose, the glycosyl transferase is at least one fucosyl-transferase and/or at least one sialyl-transferase and/or at least one N-acetyl-glucosaminyl-transferase and/or at least one galactosyl-transferase, and the glycoconjugate produced by the method is a fucosylated and/or sialylated and/or N-acetylglucosaminylated and/or galactosylated $C_6$-$C_{20}$, preferably a $C_6$-$C_{14}$, more preferably a $C_6$-$C_{10}$-alkyl O-glycoside of lactose, preferably of a human milk oligosaccharide.

Accordingly, the method even more preferably comprises:
(i) providing a genetically modified *E. coli* cell of LacZ$^-$, LacY$^+$ genotype comprising
a gene, preferably a recombinant gene encoding a fucosyl transferase enzyme that is able to transfer the fucosyl residue of an activated fucose nucleotide to an internalized acceptor molecule, and
a set of genes encoding enzymes responsible for the synthesis of the activated fucose nucleotide, preferably GDP-fucose, by a de novo pathway,
(ii) culturing the genetically modified *E. coli* cell of LacZ$^-$, LacY$^+$ genotype in the presence of an exogenous acceptor which is $C_6$-$C_{20}$, preferably a $C_6$-$C_{14}$, more preferably a $C_6$-$C_{10}$-alkyl O-glycoside of lactose, inducing
(a) internalization of the exogenous $C_6$-$C_{20}$, preferably a $C_6$-$C_{14}$, more preferably a $C_6$-$C_{10}$-alkyl O-glycoside of lactose via an active transport mechanism by a lactose permease of the genetically modified cell,
(b) formation of an activated fucose nucleotide, preferably GDP-fucose, by a de novo pathway, and
(c) formation of a $C_6$-$C_{20}$, preferably a $C_6$-$C_{14}$, more preferably a $C_6$-$C_{10}$-alkyl O-glycoside of a glycoconjugate from the internalized $C_6$-$C_{20}$, preferably a $C_6$-$C_{14}$, more preferably a $C_6$-$C_{10}$-alkyl O-glycoside of lactose by a fucosyl transfer mediated by the fucosyl transferase enzyme,
(iii) collecting the $C_6$-$C_{20}$, preferably a $C_6$-$C_{14}$, more preferably a $C_6$-$C_{10}$-alkyl O-glycoside of a glycoconjugate which is a fucosylated $C_6$-$C_{20}$, preferably a $C_6$-$C_{14}$, more preferably a $C_6$-$C_{10}$-alkyl O-glycoside of lactose, particularly $C_6$-$C_{20}$, preferably a $C_6$-$C_{14}$, more preferably a $C_6$-$C_{10}$-alkyl O-glycoside of 2'-fucosyllactose, 3-fucosyllactose or difucosyllactose, from the culture medium.

Yet even more preferably, the method comprises:
(i) providing a genetically modified *E. coli* cell of LacZ$^-$, LacY$^+$ genotype comprising
a gene, preferably a recombinant gene encoding a sialyl transferase enzyme that is able to transfer the sialyl residue of an activated sialic acid nucleotide to an internalized acceptor molecule, and
a set of genes encoding enzymes responsible for the synthesis of the activated sialic acid nucleotide, preferably CMP-sialic acid, by a de novo pathway,
(ii) culturing the genetically modified *E. coli* cell of LacZ$^-$, LacY$^+$ genotype in the presence of an exogenous acceptor which is a $C_6$-$C_{20}$, preferably a $C_6$-$C_{14}$, more preferably a $C_6$-$C_{10}$-alkyl O-glycoside of lactose, inducing
(a) internalization of the exogenous $C_6$-$C_{20}$, preferably a $C_6$-$C_{14}$, more preferably a $C_6$-$C_{10}$-alkyl O-glycoside of lactose via an active transport mechanism by a lactose permease of the genetically modified cell,
(b) formation of an activated sialic acid nucleotide, preferably CMP-sialic acid, by a de novo pathway, and
(c) formation of a $C_6$-$C_{20}$, preferably a $C_6$-$C_{14}$, more preferably a $C_6$-$C_{10}$-alkyl O-glycoside of a glycoconjugate from the internalized $C_6$-$C_{20}$, preferably a $C_6$-$C_{14}$, more preferably a $C_6$-$C_{10}$-alkyl O-glycoside of lactose by a sialyl transfer mediated by the sialyl transferase enzyme,
(iii) collecting the $C_6$-$C_{20}$, preferably a $C_6$-$C_{14}$, more preferably a $C_6$-$C_{10}$-alkyl O-glycoside of a glycoconjugate which is a sialylated $C_6$-$C_{20}$, preferably a $C_6$-$C_{14}$, more preferably a $C_6$-$C_{10}$-alkyl O-glycoside of lactose, particularly $C_6$-$C_{20}$, preferably a $C_6$-$C_{14}$, more preferably a $C_6$-$C_{10}$-alkyl O-glycoside of 3'-sialyllactose or 6'-sialyllactose, from the culture medium.

Yet even more preferably, the method comprises:
(i) providing a genetically modified *E. coli* cell of LacZ$^-$, LacY$^+$ genotype comprising
a gene, preferably a recombinant gene encoding a sialyl transferase enzyme that is able to transfer the sialyl residue of an activated sialic acid nucleotide to an internalized acceptor molecule,
a gene, preferably a recombinant gene encoding a fucosyl transferase enzyme that is able to transfer the sialyl residue of an activated sialic acid nucleotide to an internalized acceptor molecule,
a set of genes encoding enzymes responsible for the synthesis of the activated sialic acid nucleotide, preferably CMP-sialic acid, by a de novo pathway, and
a set of genes encoding enzymes responsible for the synthesis of said activated fucose nucleotide, preferably GDP-fucose, by a de novo pathway,
(ii) culturing the genetically modified *E. coli* cell of LacZ$^-$, LacY$^+$ genotype in the presence of an exogenous $C_6$-$C_{20}$, preferably a $C_6$-$C_{14}$, more preferably a $C_6$-$C_{10}$-alkyl O-glycoside of lactose, inducing
(a) internalization of the exogenous $C_6$-$C_{20}$, preferably a $C_6$-$C_{14}$, more preferably a $C_6$-$C_{10}$-alkyl O-glycoside of lactose via an active transport mechanism by a lactose permease of the genetically modified cell,
(b) formation of an activated sialic acid nucleotide, preferably CMP-sialic acid, by a de novo pathway,
(c) formation of an activated fucose nucleotide, preferably GDP-fucose, by a de novo pathway, and
(d) formation of a $C_6$-$C_{20}$, preferably a $C_6$-$C_{14}$, more preferably a $C_6$-$C_{10}$-alkyl O-glycoside of a glycoconjugate from the internalized $C_6$-$C_{20}$, preferably a $C_6$-$C_{14}$, more preferably a $C_6$-$C_{10}$-alkyl O-glycoside of lactose by a sialyl transfer mediated by the sialyl transferase enzyme, and by a fucosyl transfer mediated by the fucosyl transferase enzyme, (iii) collecting the $C_6$-$C_{20}$, preferably a $C_6$-$C_{14}$, more preferably a $C_6$-$C_{10}$-alkyl O-glycoside of a glycoconjugate which is a sialylated and fucosylated $C_6$-$C_{20}$, preferably a $C_6$-$C_{14}$, more preferably a $C_6$-$C_{10}$-alkyl O-glycoside of lactose, particularly $C_6$-$C_{20}$, preferably a $C_6$-$C_{14}$, more preferably a $C_6$-$C_{10}$-alkyl O-glycoside of 3'-sialyl-3-fucosyllactose, from the culture medium.

Yet even more preferably, the method comprises:

(i) providing a genetically modified E. coli cell of LacZ⁻, LacY⁺ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and optionally a set of genes encoding enzymes responsible for the synthesis of the activated Gal nucleotide, preferably UDP-Gal, by a de novo pathway, (ii) culturing the genetically modified E. coli cell of LacZ⁻, LacY⁺ genotype in the presence of an exogenous $C_6$-$C_{20}$, preferably a $C_6$-$C_{14}$, more preferably a $C_6$-$C_{10}$-alkyl O-glycoside of lactose, inducing (a) internalization of the exogenous $C_6$-$C_{20}$, preferably a $C_6$-$C_{14}$, more preferably a $C_6$-$C_{10}$-alkyl O-glycoside of lactose derivative via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the $C_6$-$C_{20}$, preferably a $C_6$-$C_{14}$, more preferably a $C_6$-$C_{10}$-alkyl O-glycoside of a glycoconjugate from the internalized $C_6$-$C_{20}$, preferably a $C_6$-$C_{14}$, more preferably a $C_6$-$C_{10}$-alkyl O-glycoside of lactose by a N-acetylglucosaminyl transfer mediated by the N-acetylglucosaminyl transferase enzyme optionally followed by a galactosyl transfers mediated by the galactosyl transferase enzyme, (iii) collecting the $C_6$-$C_{20}$, preferably a $C_6$-$C_{14}$, more preferably a $C_6$-$C_{10}$-alkyl O-glycoside of a glycoconjugate which is an N-acetylglucosaminylated $C_6$-$C_{20}$, preferably a $C_6$-$C_{14}$, more preferably a $C_6$-$C_{10}$-alkyl O-glycoside of lactose optionally substituted by galactose, particularly $C_6$-$C_{20}$, preferably a $C_6$-$C_{14}$, more preferably a $C_6$-$C_{10}$-alkyl O-glycoside of 3'-N-acetylglucosaminyl lactose, LNT or LNnT, from the culture medium.

The most preferred way to carry out the fifth particular embodiment of the invention comprises:

(i) providing a genetically modified E. coli cell of LacZ⁻, LacY⁺ genotype comprising a recombinant gene encoding an α-1,2-fucosyl transferase, and a set of genes encoding enzymes responsible for the synthesis of GDP-fucose by a de novo pathway, (ii) culturing the genetically modified E. coli cell of LacZ⁻, LacY⁺ genotype in the presence of an exogenous $C_6$-$C_{20}$, preferably a $C_6$-$C_{14}$, more preferably a $C_6$-$C_{10}$-alkyl O-glycoside of lactose, inducing (a) internalization of the exogenous $C_6$-$C_{20}$, preferably a $C_6$-$C_{14}$, more preferably a $C_6$-$C_{10}$-alkyl O-glycoside of lactose via an active transport mechanism by a lactose permease of the genetically modified cell, (b) formation of GDP-fucose by a de novo pathway, and (c) formation of a glycoconjugate from the internalized $C_6$-$C_{20}$, preferably a $C_6$-$C_{14}$, more preferably a $C_6$-$C_{10}$-alkyl O-glycoside of lactose by a fucosyl transfer mediated by the α-1,2-fucosyl transferase, (iii) collecting the glycoconjugate which is a $C_6$-$C_{20}$, preferably a $C_6$-$C_{14}$, more preferably a $C_6$-$C_{10}$-alkyl O-glycoside of 2'-fucosyllactose, from the culture medium.

According to a sixth particular embodiment, it is provided a method for producing a glycoconjugate of interest having an oligosaccharide part covalently linked to polyethylene glycol using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to polyethylene glycol inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a mono- or disaccharide part covalently linked to polyethylene glycol as defined above, and the glycoconjugate of interest is of an oligosaccharide part covalently linked to polyethylene glycol as defined above.

Also preferably with regard to the sixth particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous acceptor that is a mono- or disaccharide part covalently linked to polyethylene glycol inducing (a) internalization of the exogenous acceptor molecule via an active and/or passive transport mechanism by the genetically modified cell, (b) formation of the activated sugar nucleotide by a de novo pathway, and (c) formation of the glycoconjugate from the internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous acceptor molecule is selected from galactose, glucose, N-acetyl-glucosamine and lactose, more preferably lactose. In this regard, a preferred exogenous acceptor can be characterized by formula 7

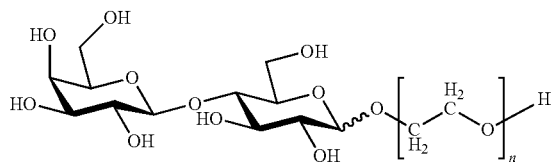

7 wherein n is an integer from 1 to 10, preferably from 2 to 6.

According to an even more preferable way to perform this sixth particular embodiment of the present invention, the genetically modified cell is *E. coli* of LacZ⁻, LacY⁺ genotype, the exogenous acceptor is a compound of formula 7, the glycosyl transferase is at least one fucosyl-transferase and/or at least one sialyl-transferase and/or at least one N-acetylglucosaminyl-transferase, and/or at least one galactosyl-transferase and the glycoconjugate produced by the method is a fucosylated and/or sialylated and/or N-acetylglucosaminylated and/or galactosylated compound of formula 7, preferably polyethylene glycol O-glycoside of a human milk oligosaccharide of formula 7a

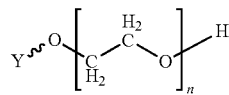

7a wherein Y is a human milk oligosaccharide glycosyl residue, and n is as defined above.

Accordingly, the method even more preferably comprises:
(i) providing a genetically modified *E. coli* cell of LacZ⁻, LacY⁺ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified *E. coli* cell of LacZ⁻, LacY⁺ genotype in the presence of an exogenous lactose derivative of formula 7, inducing (a) internalization of the exogenous lactose derivative of formula 7 via an active transport mechanism by a lactose permease of the genetically modified cell, (b) formation of an activated fucose nucleotide, preferably GDP-fucose, by a de novo pathway, and (c) formation of a glycoconjugate from the internalized lactose derivative of formula 7 by a fucosyl transfer mediated by the fucosyl transferase enzyme, (iii) collecting a fucosylated lactose derivative of formula 7, particularly a corresponding polyethylene glycol O-glycoside of 2'-fucosyllactose, 3-fucosyllactose or difucosyllactose, from the culture medium.

Yet even more preferably, the method comprises:
(i) providing a genetically modified *E. coli* cell of LacZ⁻, LacY⁺ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified *E. coli* cell of LacZ⁻, LacY⁺ genotype in the presence of an exogenous lactose derivative of formula 7, inducing (a) internalization of the exogenous lactose derivative of formula 7 via an active transport mechanism by a lactose permease of the genetically modified cell, (b) formation of an activated sialic acid nucleotide, preferably CMP-sialic acid, by a de novo pathway, and (c) formation of a glycoconjugate from the internalized lactose derivative of formula 7 by a sialyl transfer mediated by the sialyl transferase enzyme, (iii) collecting the sialylated lactose derivative of formula 7, particularly a corresponding polyethylene glycol O-glycoside of 3'-sialyllactose or 6'-sialyllactose, from the culture medium.

Yet even more preferably, the method comprises:
(i) providing a genetically modified *E. coli* cell of LacZ⁻, LacY⁺ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of said activated fucose nucleotide, preferably GDP-fucose, by a de novo pathway, (ii) culturing the genetically modified *E. coli* cell of LacZ⁻, LacY⁺ genotype in the presence of an exogenous lactose derivative of formula 7, inducing (a) internalization of the exogenous lactose derivative of formula 7 via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized lactose derivative of formula 7 by a sialyl transfer mediated by the sialyl transferase enzyme, and by a fucosyl transfer mediated by the fucosyl transferase enzyme, (iii) collecting the sialylated and fucosylated lactose derivative of formula 7, particularly the corresponding polyethylene glycol O-glycoside of 3'-sialyl-3-fucosyllactose, from the culture medium.

Yet even more preferably, the method comprises:

(i) providing a genetically modified $E.$ $coli$ cell of LacZ$^-$, LacY$^+$ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and optionally a set of genes encoding enzymes responsible for the synthesis of the activated Gal nucleotide, preferably UDP-Gal, by a de novo pathway, (ii) culturing the genetically modified $E.$ $coli$ cell of LacZ$^-$, LacY$^+$ genotype in the presence of an exogenous lactose derivative of formula 7, inducing (a) internalization of the exogenous lactose derivative of formula 7 via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of a glycoconjugate from the internalized lactose derivative of formula 7 by a N-acetylglucosaminyl transfer mediated by the N-acetylglucosaminyl transferase enzyme optionally followed by a galactosyl transfers mediated by the galactosyl transferase enzyme, (iii) collecting the N-acetylglucosaminylated lactose derivative of formula 7 optionally substituted by galactose, particularly the corresponding polyethylene glycol O-glycoside of 3'-N-acetylglucosaminyl lactose, LNT or LNnT, from the culture medium.

The most preferred way to carry out the sixth particular embodiment of the invention comprises:

(i) providing a genetically modified $E.$ $coli$ cell of LacZ$^-$, LacY$^+$ genotype comprising a recombinant gene encoding an α-1,2-fucosyl transferase, and a set of genes encoding enzymes responsible for the synthesis of GDP-fucose by a de novo pathway, (ii) culturing the genetically modified $E.$ $coli$ cell of LacZ$^-$, LacY$^+$ genotype in the presence of an exogenous lactose derivative of formula 7, inducing (a) internalization of the exogenous lactose derivative of formula 7 via an active transport mechanism by a lactose permease of the genetically modified cell, (b) formation of GDP-fucose by a de novo pathway, and (c) formation of a glycoconjugate from the lactose derivative of formula 7 by a fucosyl transfer mediated by the α-1,2-fucosyl transferase, (iii) collecting the corresponding polyethylene glycol O-glycoside of 2'-fucosyllactose, from the culture medium.

According to a seventh particular embodiment, it is provided a method for producing a glycoconjugate of interest having an oligosaccharide part covalently linked to an α,β-unsaturated amido group using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to an α,β-unsaturated amido group inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The α,β-unsaturated amido group is preferably a group of formula A defined above, more preferably $Q_1$, $Q_2$, $Q_3$ and $Q_4$ in group A are, independently, H and methyl, even more preferably H (that is group A is acrylamido).

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a mono- or disaccharide attached to moiety A with its anomeric carbon atom, preferably $Q_1$, $Q_2$, $Q_3$ and $Q_4$ in group A are, independently, H and methyl, even more preferably H, and the glycoconjugate produced is an oligosaccharide attached to moiety A with its anomeric carbon atom, preferably $Q_1$, $Q_2$, $Q_3$ and $Q_4$ in group A are, independently, H and methyl, even more preferably H.

Also preferably with regard to the seventh particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous mono- or disaccharide attached to moiety A with its anomeric carbon atom, preferably $Q_1$, $Q_2$, $Q_3$ and $Q_4$ in group A are, independently, H and methyl, even more preferably H, inducing (a) internalization of the exogenous mono- or disaccharide attached to moiety A with its anomeric carbon atom, preferably $Q_1$, $Q_2$, $Q_3$ and $Q_4$ in group A are, independently, H and methyl, even more preferably H via an active and/or passive transport mechanism by the genetically modified cell, (b) formation of the activated sugar nucleotide by a de novo pathway, and (c) formation of an oligosaccharide attached to moiety A with its anomeric carbon atom, preferably $Q_1$, $Q_2$, $Q_3$ and $Q_4$ in group A are, independently, H and methyl, even more preferably H, from the internalized mono- or disaccharide attached to moiety A with its anomeric carbon atom, preferably $Q_1$, $Q_2$, $Q_3$ and $Q_4$ in group A are, independently, H and methyl, even more preferably H, by a glycosyl transfers mediated by the glycosyl transferase enzyme, (iii) collecting the oligosaccharide attached to moiety A with its anomeric carbon atom, preferably $Q_1$, $Q_2$, $Q_3$ and $Q_4$ in group A are, independently, H and methyl, even more preferably H, from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous acceptor defined above is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is a glycosylated galactose, glucose, N-acetyl-glucosamine or lactose, more preferably lactose, attached to moiety A with its anomeric carbon atom, preferably $Q_1$, $Q_2$, $Q_3$ and $Q_4$ in group A are, independently, H and methyl, even more preferably H.

According to an even more preferable way to perform this seventh particular embodiment of the present invention, the genetically modified cell is E. coli of LacZ$^-$, LacY$^+$ genotype, the exogenous acceptor is a compound of formula 9

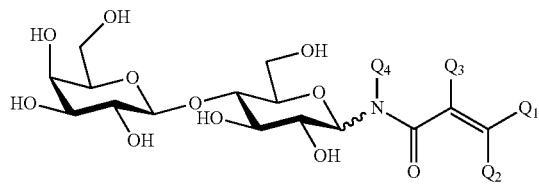

9 wherein $Q_1$, $Q_2$, $Q_3$ and $Q_4$ are, independently, H and methyl, even more preferably the glycosyl transferase is at least one fucosyl-transferase and/or at least one sialyl-transferase and/or at least one N-acetylglucosaminyl-transferase and/or one galactosyl-transferase, and the glycoconjugate produced by the method is a fucosylated and/or sialylated and/or N-acetylglucosaminylated and/or galactosylated compound of formula 9, preferably a compound of formula 9a

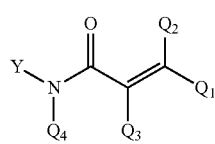

9a wherein Y is a human milk oligosaccharide glycosyl residue, and $Q_1$, $Q_2$, $Q_3$ and $Q_4$ are as defined above.

Accordingly, the method even more preferably comprises:

(i) providing a genetically modified E. coli cell of LacZ$^-$, LacY$^+$ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified E. coli cell of LacZ$^-$, LacY$^+$ genotype in the presence of an exogenous lactose derivative of formula 9, inducing (a) internalization of the exogenous lactose derivative of formula 9, via an active transport mechanism by a lactose permease of the genetically modified cell, (b) formation of an activated fucose nucleotide, preferably GDP-fucose, by a de novo pathway, and (c) formation of a glycoconjugate from the internalized lactose derivative of formula 9 by a fucosyl transfer mediated by the fucosyl transferase enzyme, (iii) collecting the fucosylated lactose derivative of formula 9, particularly a compound of formula 9a, wherein Y is a glycosyl residue of 2'-fucosyllactose, 3-fucosyllactose or difucosyllactose, and $Q_1$, $Q_2$, $Q_3$ and $Q_4$ are as defined above, from the culture medium.

Yet even more preferably, the method comprises:

(i) providing a genetically modified E. coli cell of LacZ$^-$, LacY$^+$ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified E. coli cell of LacZ$^-$, LacY$^+$ genotype in the presence of an exogenous lactose derivative of formula 9, inducing (a) internalization of the exogenous lactose derivative of formula 9 via an active transport mechanism by a lactose permease of the genetically modified cell, (b) formation of an activated sialic acid nucleotide, preferably CMP-sialic acid, by a de novo pathway, and (c) formation of a glycoconjugate from the internalized lactose derivative of formula 9 by a sialyl transfer mediated by the sialyl transferase enzyme, (iii) collecting the sialylated lactose derivative of formula 9, particularly a compound of formula 9a wherein Y is a glycosyl residue of 3'-sialyllactose or 6'-sialyllactose, and $Q_1$, $Q_2$, $Q_3$ and $Q_4$ are as defined above, from the culture medium.

Yet even more preferably, the method comprises:

(i) providing a genetically modified E. coli cell of LacZ$^-$, LacY$^+$ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of said activated fucose nucleotide, preferably GDP-fucose, by a de novo pathway, (ii) culturing the genetically modified *E. coli* cell of LacZ$^-$, LacY$^+$ genotype in the presence of an exogenous lactose derivative of formula 9, inducing (a) internalization of the exogenous lactose derivative of formula 9 via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized lactose derivative of formula 9 by a sialyl transfer mediated by the sialyl transferase enzyme, and by a fucosyl transfer mediated by the fucosyl transferase enzyme, (iii) collecting the sialylated and fucosylated lactose derivative of formula 9, particularly a compound of formula 9a wherein Y is a glycosyl residue of 3'-sialyl-3-fucosyllactose, and $Q_1$, $Q_2$, $Q_3$ and $Q_4$ are as defined above, from the culture medium.

Yet even more preferably, the method comprises:

(i) providing a genetically modified *E. coli* cell of LacZ$^-$, LacY$^+$ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and optionally a set of genes encoding enzymes responsible for the synthesis of the activated Gal nucleotide, preferably UDP-Gal, by a de novo pathway, (ii) culturing the genetically modified *E. coli* cell of LacZ$^-$, LacY$^+$ genotype in the presence of an exogenous lactose derivative of formula 9, inducing (a) internalization of the exogenous lactose derivative of formula 9 via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of a glycoconjugate by a N-acetylglucosaminyl transfer mediated by the N-acetylglucosaminyl transferase enzyme optionally followed by a galactosyl transfer mediated by the galactosyl transferase enzyme, (iii) collecting the N-acetylglucosaminylated lactose derivative of formula 9 optionally substituted by a galactose, particularly a compound of formula 9a wherein Y is a glycosyl residue of LNT or LNnT, and $Q_1$, $Q_2$, $Q_3$ and $Q_4$ are as defined above, from the culture medium.

The most preferred way to carry out the seventh particular embodiment of the invention comprises:

(i) providing a genetically modified *E. coli* cell of LacZ$^-$, LacY$^+$ genotype comprising a recombinant gene encoding an α-1,2-fucosyl transferase, and a set of genes encoding enzymes responsible for the synthesis of GDP-fucose by a de novo pathway, (ii) culturing the genetically modified *E. coli* cell of LacZ$^-$, LacY$^+$ genotype in the presence of an exogenous lactose derivative of formula 9, inducing (a) internalization of the exogenous lactose derivative of formula 9 by a lactose permease of the genetically modified cell, (b) formation of GDP-fucose by a de novo pathway, and (c) formation of a glycoconjugate from the internalized lactose derivative of formula 9 by a fucosyl transfer mediated by the α-1,2-fucosyl transferase, (iii) collecting the compound of formula 9a wherein Y is a glycosyl residue of 2'-fucosyllactose, and $Q_1$, $Q_2$, $Q_3$ and $Q_4$ are as defined above, from the culture medium.

According to a eighth particular embodiment, it is provided a method for producing a glycoconjugate of interest having an oligosaccharide part covalently linked to polyvinyl alcohol using a genetically modified cell, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, (ii) culturing the genetically modified cell in the presence of an exogenous acceptor having a mono- or disaccharide part covalently linked to polyvinyl alcohol inducing (a) internalization of the exogenous acceptor molecule via an active and/or passive transport mechanism by the genetically modified cell, and (b) formation of the glycoconjugate from the internalized acceptor molecule by a glycosyl transfer mediated by the glycosyl transferase enzyme expressed by the cell, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, and the glycoconjugate is formed from the internalized acceptor by multiple glycosyl transfer mediated by multiple glycosyl transferases expressed by the cell.

In a more preferred embodiment the exogenous acceptor is a mono- or disaccharide part covalently linked to polyvinyl alcohol as defined above, and the glycoconjugate of interest is an oligosaccharide part covalently linked to polyvinyl alcohol as defined above.

Also preferably with regard to the eighth particular embodiment, the method comprises:

(i) providing a genetically modified cell comprising a gene, preferably a recombinant gene encoding a glycosyl transferase enzyme that is able to transfer the glycosyl residue of an activated sugar nucleotide to an internalized acceptor molecule, and a set of genes encoding enzymes responsible for the synthesis of the activated sugar nucleotide by a de novo pathway, (ii) culturing the genetically modified cell in the presence of an exogenous acceptor that is a mono- or disaccharide part covalently linked to polyvinyl alcohol inducing (a) internalization of the exogenous acceptor molecule via an active and/or passive transport mechanism by the genetically modified cell, (b) formation of the activated sugar nucleotide by a de novo pathway, and (c) formation of the glycoconjugate from the internalized acceptor molecule by a glycosyl transfers mediated by the glycosyl transferase enzyme, (iii) collecting the glycoconjugate from the culture medium.

The genetically modified cell can comprise more than one gene, preferably more than one recombinant gene, encoding more than one glycosyl transferase enzyme that are able to transfer the glycosyl residue of activated sugar nucleotides to an internalized acceptor molecule or glycosylated derivative thereof, as well as it can comprise more than one set of genes encoding set of enzymes responsible for the synthesis of more than one activated sugar nucleotide by a de novo pathway, and the glycoconjugate is formed from the internalized acceptor by multiple glycosyl transfer mediated by multiple glycosyl transferases expressed by the cell.

In a more preferred realization the genetically modified cell lacks enzymes able to degrade the internalized acceptor molecule or glycosylated derivative thereof.

Also more preferably, the mono- or disaccharide part of the exogenous acceptor molecule is selected from galactose, glucose, N-acetyl-glucosamine and lactose, more preferably lactose, the internalization of the above defined exogenous acceptor takes place via an active transport mechanism mediated by a permease, preferably a lactose permease, and the product of the fermentation is selected from a glycosylated galactose, glucose, N-acetyl-glucosamine and lactose covalently linked to polyvinyl alcohol, more preferably glycosylated lactose covalently linked to polyvinyl alcohol.

According to an even more preferable way performing this eighth particular embodiment of the present invention, the genetically modified cell is $E.\ coli$ of $LacZ^-$, $LacY^+$ genotype, the exogenous acceptor is lactose covalently linked to polyvinyl alcohol, the glycosyl transferase is at least one fucosyl-transferase and/or at least one sialyl-transferase and/or at least one N-acetylglucosaminyl-transferase and/or one galactosyl-transferase, and the glycoconjugate of interest produced by the method is a fucosylated and/or sialylated and/or N-acetylglucosaminylated and/or galactosylated lactose, preferably a human milk oligosaccharide, covalently linked to polyvinyl alcohol.

Accordingly, the method most preferably comprises:

(i) providing a genetically modified $E.\ coli$ cell of $LacZ^-$, $LacY^+$ genotype comprising a gene, preferably a recombinant gene encoding a fucosyl transferase enzyme that is able to transfer the fucosyl residue of an activated fucose nucleotide to an internalized acceptor molecule, and a set of genes encoding enzymes responsible for the synthesis of the activated fucose nucleotide, preferably GDP-fucose, by a de novo pathway, (ii) culturing the genetically modified $E.\ coli$ cell of $LacZ^-$, $LacY^+$ genotype in the presence of an exogenous acceptor that is lactose covalently linked to polyvinyl alcohol inducing (a) internalization of the exogenous lactose acceptor derivative via an active transport mechanism by a lactose permease of the genetically modified cell, (b) formation of an activated fucose nucleotide, preferably GDP-fucose, by a de novo pathway, and (c) formation of a glycoconjugate from the internalized lactose acceptor derivative by a fucosyl transfer mediated by the fucosyl transferase enzyme, (iii) collecting the glycoconjugate that is a fucosylated lactose, preferably 2'-fucosyllactose, 3-fucosyllactose or difucosyllactose, covalently linked to polyvinyl alcohol from the culture medium.

Moreover, the method most preferably comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, and a set of genes encoding enzymes responsible for the synthesis of the activated sialic acid nucleotide, preferably CMP-sialic acid, by a de novo pathway, (ii) culturing the genetically modified $E.\ coli$ cell of $LacZ^-$, $LacY^+$ genotype in the presence of an exogenous acceptor that is lactose covalently linked to polyvinyl alcohol inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, and (c) formation of a glycoconjugate from the internalized lactose acceptor derivative by a sialyl transfer mediated by the sialyl transferase enzyme, (iii) collecting the glycoconjugate that is a sialylated lactose, preferably 3'-sialyllactose or 6'-sialyllactose, covalently linked to polyvinyl alcohol from the culture medium.

In addition, the method most preferably comprises:

(i) providing a genetically modified $E.\ coli$ cell of $LacZ^-$, $LacY^+$ genotype comprising a gene, preferably a recombinant gene encoding a sialyl transferase enzyme that is able to transfer the sialyl residue of an activated sialic acid nucleotide to an internalized acceptor molecule, a gene, preferably a recombinant gene encoding a fucosyl transferase enzyme that is able to transfer the sialyl residue of an activated sialic acid nucleotide to an internalized acceptor molecule, a set of genes encoding enzymes responsible for the synthesis of the activated sialic acid nucleotide, preferably CMP-sialic acid, by a de novo pathway, and a set of genes encoding enzymes responsible for the synthesis of the activated fucose nucleotide, preferably GDP-fucose, by a de novo pathway, (ii) culturing the genetically modified $E.\ coli$ cell of $LacZ^-$, $LacY^+$ genotype in the presence of an exogenous acceptor that is lactose covalently linked to polyvinyl alcohol inducing (a) internalization of the exogenous lactose acceptor derivative via an active transport mechanism by a lactose permease of the genetically modified cell, (b) formation of an activated sialic acid nucleotide, preferably CMP-sialic acid, by a de novo pathway, (c) formation of an activated fucose nucleotide, preferably GDP-fucose, by a de novo pathway, and (d) formation of a glycoconjugate from the internalized lactose acceptor derivative by a sialyl transfer mediated by the sialyl transferase enzyme, and by a fucosyl transfer mediated by the fucosyl transferase enzyme, (iii) collecting the glycoconjugate that is a sialylated fucosylated lactose, preferably 3'-sialyl-3-fucosyllactose, covalently linked to polyvinyl alcohol from the culture medium.

Furthermore, the method most preferably comprises:

(i) providing a genetically modified $E.\ coli$ cell of $LacZ^-$, $LacY^+$ genotype comprising a gene, preferably a recombinant gene encoding a N-acetylglucosaminyl transferase enzyme that is able to transfer the N-acetylglucosaminyl residue of an activated GlcNAc nucleotide to an internalized acceptor molecule, optionally a gene, preferably a recombinant gene encoding a galactosyl transferase enzyme that is able to transfer the galactosyl residue of an activated Gal nucleotide to an internalized acceptor molecule, a set of genes encoding enzymes responsible for the synthesis of the activated GlcNAc nucleotide, preferably UDP-GlcNAc, by a de novo pathway, and a set of genes encoding enzymes responsible for the synthesis of the activated Gal nucleotide, preferably UDP-Gal, by a de novo pathway, (ii) culturing the genetically modified *E. coli* cell of LacZ$^-$, LacY$^+$ genotype in the presence of an exogenous acceptor that is lactose covalently linked to polyvinyl alcohol inducing (a) internalization of the exogenous lactose derivative via an active transport mechanism by a lactose permease of the genetically modified cell, (b) formation of an activated GlcNAc nucleotide, preferably UDP-GlcNAc, by a de novo pathway, (c) optional formation of an activated Gal nucleotide, preferably UDP-Gal, by a de novo pathway, and (d) formation of the glycoconjugate of interest from the internalized lactose derivative by a N-acetylglucosaminyl transfer mediated by the N-acetylglucosaminyl transferase enzyme optionally followed by a galactosyl transfers mediated by the galactosyl transferase enzyme, (iii) collecting the glycoconjugate that is an N-acetylglucosaminylated lactose optionally substituted by galactose and covalently linked to polyvinyl alcohol, preferably 3'-N-acetylglucosaminyl lactose, LNT or LNnT covalently linked to polyvinyl alcohol from the culture medium.

The present invention also relates to providing glycoconjugates having an oligosaccharide part covalently linked to a non-sugar moiety selected from the group consisting of amino acids, peptides, proteins, lipids, longer alkyl groups, polyethylene glycols, α,β-unsaturated amido group and polyvinyl alcohols. Preferably, the above-mentioned glycoconjugates are O-, N- or S-glycosides. More preferably, the oligosaccharide moiety comprises monosaccharide units selected from the group consisting of glucose, galactose, N-acetylglucosamine, fucose and sialic acid. Even more preferably, the oligosaccharide residue is a lactose moiety substituted by fucose and/or N-acetylglucosamine and/or galactose and/or sialic acid. Accordingly, the oligosaccharide moiety of the above defined glycoconjugates are characterized by formula 1

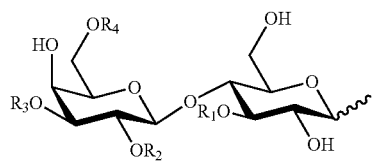

wherein $R_1$ is fucosyl or $R_2$ is fucosyl or $R_3$ is selected from H, sialyl, N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue, $R_4$ is selected from H, sialyl and N-acetyl-lactosaminyl groups optionally substituted with a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue, and provided that at least one of the $R_1$, $R_2$, $R_3$ and $R_4$ groups is different from H, by culturing, as disclosed above, lactose covalently linked to a non-sugar moiety selected from the group consisting of amino acids, peptides, proteins, lipids, longer alkyl groups, polyethylene glycols, α,β-unsaturated amido group and polyvinyl alcohols.

Preferably, the moiety of formula 1 can be characterized by formula 1a, 1b or 1c

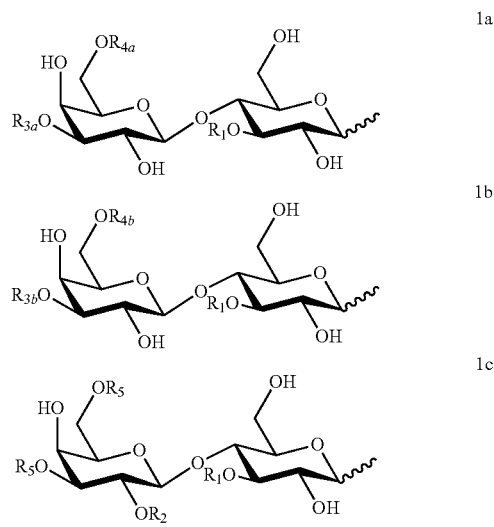

wherein $R_1$ and $R_2$ are as defined above, $R_{3a}$ is an N-acetyl-lactosaminyl group optionally substituted with a glycosyl residue comprising one N-acetyl-lactosaminyl and/or one lacto-N-biosyl group; each of the N-acetyl-lactosaminyl and lacto-N-biosyl groups can be substituted with one or more sialyl and/or fucosyl residue, $R_{4a}$ is H or an N-acetyl-lactosaminyl group optionally substituted with a lacto-N-biosyl group; each of the N-acetyl-lactosaminyl and lacto-N-biosyl groups can be substituted with one or more sialyl and/or fucosyl residue, $R_{3b}$ is a lacto-N-biosyl group optionally substituted with one or more sialyl and/or fucosyl residue(s), $R_{4b}$ is H or an N-acetyl-lactosaminyl group optionally substituted with one or two N-acetyl-lactosaminyl and/or one lacto-N-biosyl groups; each of the N-acetyl-lactosaminyl and lacto-N-biosyl groups can be substituted with one or more sialyl and/or fucosyl residues, $R_5$ is, independently, H or sialyl, and wherein at least one of $R_1$, $R_2$ or $R_5$ is not H.

More preferably, the moieties according to formulae 1a or 1b are characterized in that:

the N-acetyl-lactosaminyl group in the glycosyl residue of $R_{3a}$ is attached to another N-acetyl-lactosaminyl group with a 1-3 interglycosidic linkage, the lacto-N-biosyl group in the glycosyl residue of $R_{3a}$ is attached to the N-acetyl-lactosaminyl group with a 1-3 interglycosidic linkage, the lacto-N-biosyl group in the glycosyl residue of $R_{4a}$ is attached to the N-acetyl-lactosaminyl group with a 1-3 interglycosidic linkage, the N-acetyl-lactosaminyl group in the glycosyl residue of $R_{4b}$ is attached to another N-acetyl-lactosaminyl group with a 1-3 or a 1-6 interglycosidic linkage, the lacto-N-biosyl group in the glycosyl residue of $R_{4b}$ is attached to the N-acetyl-lactosaminyl group with a 1-3 interglycosidic linkage.

More preferably, the moieties according to formulae 1a, 1b and 1c are human milk oligosaccharide (HMO) glycosyl groups.

Also more preferably, the moiety of formula 1a is a glycosyl residue of lacto-N-neotetraose, para-lacto-N-hexaose, para-lacto-N-neohexaose, lacto-N-neohexaose, para-lacto-N-octaose or lacto-N-neooctaose optionally substituted with one or more sialyl and/or fucosyl residue, and the moiety of formula 1b is a glycosyl residue of lacto-N-tetraose, lacto-N-hexaose, lacto-N-octaose, iso-lacto-N-octaose, lacto-N-decaose or lacto-N-neodecaose optionally substituted with one or more sialyl and/or fucosyl residue.

Preferably, the moieties of formula 1a or 1b are characterized in that:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

According to a further preferred aspect, the moieties according to subformulae 1a, 1b or 1c may be selected from the group of: a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, or salts thereof. The glycosides may be alpha or beta-anomers, but preferably beta-anomers. Especially is preferred a residue of formula 1d

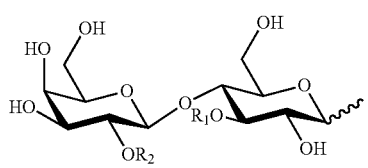

wherein $R_1$ is fucosyl or H, and $R_2$ is fucosyl or H, provided that at least one of the $R_1$ and $R_2$ groups is fucosyl.

According to a preferred realization of the invention, the glycoconjugate obtainable by the method is an oligosaccharide covalently linked to an amino acid as described by the first particular embodiment above. Preferably, the oligosaccharide is linked to serine, threonine or hydroxyproline by an O-glycosidic linkage. More preferably, the glycoconjugate covalently linked to serine or threonine, and salts thereof, obtainable by the first particular embodiment, is characterized by formula 2

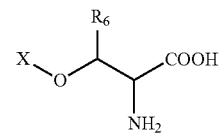

wherein X is the moiety of formula 1 as defined above, and $R_6$ is H or methyl,
by culturing, as disclosed in the first particular embodiment, a lactose derivative of formula 3

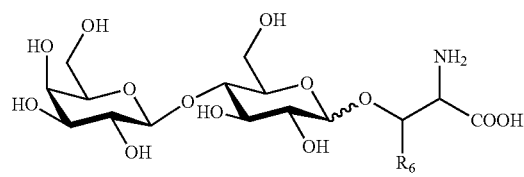

wherein $R_6$ is as defined above.

Preferably, in a compound of formula 2 moiety X is a group of formula 1a, 1b or 1c as defined above, thus to form a compound of formula 2a, 2b or 2c, respectively,

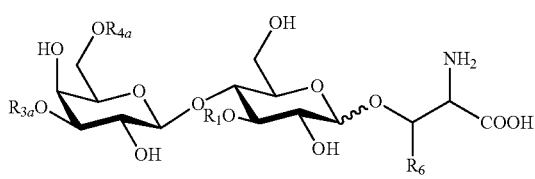

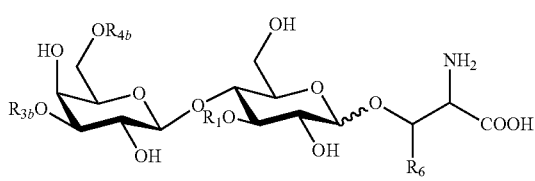

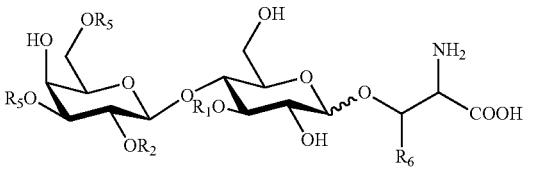

wherein $R_1$, $R_2$, $R_{3a}$, $R_{3b}$, $R_{4a}$, $R_{4b}$, $R_5$ and $R_6$ are as defined above.

More preferably, the compounds according to formulae 2a, 2b and 2c are human milk oligosaccharide (HMO) glycosyl groups.

Also more preferably, the compound of formula 2a has a glycosyl residue of lacto-N-neotetraose, para-lacto-N- hexaose, para-lacto-N-neohexaose, lacto-N-neohexaose, para-lacto-N-octaose or lacto-N-neooctaose optionally substituted with one or more sialyl and/or fucosyl residue, and the compound of formula 2b has a glycosyl residue of lacto-N-tetraose, lacto-N-hexaose, lacto-N-octaose, iso-lacto-N-octaose, lacto-N-decaose or lacto-N-neodecaose optionally substituted with one or more sialyl and/or fucosyl residue. Even more preferably, the glycosyl residue of compounds according to subformulae 2a, 2b or 2c may be selected from the group of a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, more preferably from the group of a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose and lacto-N-neotetraose, or salts thereof. The glycosides may be alpha or beta-anomers, but preferably beta-anomers. Especially is preferred a compound of formula 2d

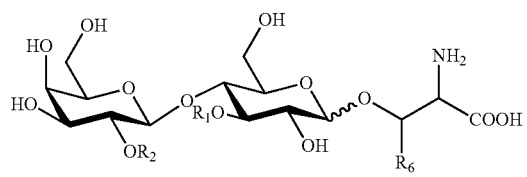

2d wherein $R_1$ is fucosyl or H, $R_2$ is fucosyl or H, and $R_6$ is H or methyl, provided that at least one of the $R_1$ and $R_2$ groups is fucosyl.

According to another preferred realization of the invention, the glycoconjugate obtainable by the method is an oligosaccharide covalently linked to a longer alkyl group as described by the fifth particular embodiment above. Preferably, the oligosaccharide is linked to an alkyl group preferably consisting of 6-24, preferably 6-20, more preferably 6-14, particularly 6-10 carbon atoms, by an O-glycosidic linkage. More preferably, the glycoconjugate covalently linked to a longer alkyl group, obtainable by the fifth particular embodiment, is characterized by formula 4

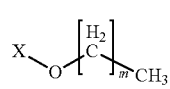

4 wherein X is the moiety of formula 1 as defined above, and m is an integer from 5-23, preferably 5-19, more preferably 5-13, particularly 5-9, by culturing, as disclosed in the fifth particular embodiment, a lactose derivative of formula 5

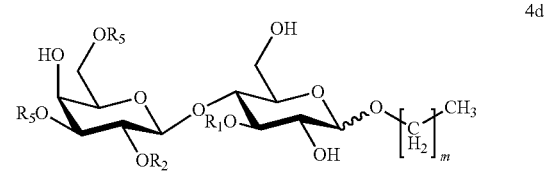

5 wherein m is as defined above.

Preferably, in a compound of formula 4 moiety X is a group of formula 1a, 1b or 1c as defined above, thus to form a compound of formula 4a, 4b or 4c, respectively,

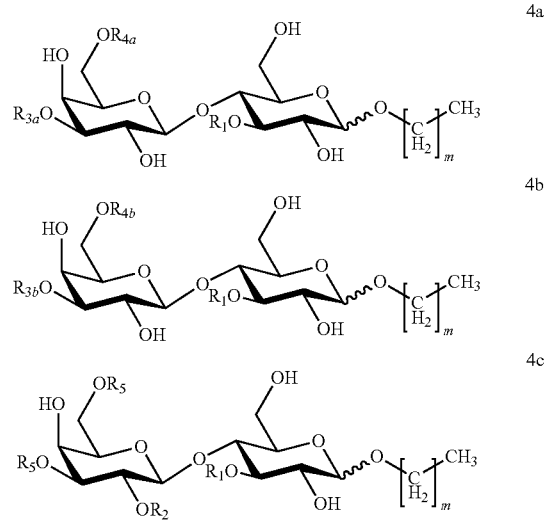

wherein $R_1$, $R_2$, $R_{3a}$, $R_{3b}$, $R_{4a}$, $R_{4b}$, $R_5$ and m are as defined above.

More preferably, the compounds according to formulae 4a, 4b and 4c are human milk oligosaccharide (HMO) glycosyl groups.

Also more preferably, the compound of formula 4a has a glycosyl residue of lacto-N-neotetraose, para-lacto-N-hexaose, para-lacto-N-neohexaose, lacto-N-neohexaose, para-lacto-N-octaose or lacto-N-neooctaose optionally substituted with one or more sialyl and/or fucosyl residue, and the compound of formula 4b has a glycosyl residue of lacto-N-tetraose, lacto-N-hexaose, lacto-N-octaose, iso-lacto-N-octaose, lacto-N-decaose or lacto-N-neodecaose optionally substituted with one or more sialyl and/or fucosyl residue. Even more preferably, the glycosyl residue of compounds according to subformulae 4a, 4b or 4c may be selected from the group of: a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, more preferably from the group of a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose and lacto-N-neotetraose, or salts thereof. The glycosides may be alpha or beta-anomers, but preferably beta-anomers. Especially is preferred a compound of formula 4d wherein R₁ is fucosyl or H, R₂ is fucosyl or H, and m is 6-10, provided that at least one of the R₁ and R₂ groups is fucosyl.

According to another preferred realization of the invention, the glycoconjugate obtainable by the method is an oligosaccharide covalently linked to a polyethylene glycol as described by the sixth particular embodiment above. Preferably, the glycoconjugate covalently linked to a polyethylene glycol, obtainable by the sixth particular embodiment, is characterized by formula 6

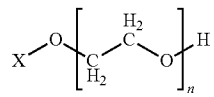
6 wherein X is the moiety of formula 1 as defined above, and n is an integer from 1 to 10, preferably 2 to 6, by culturing, as disclosed in the sixth particular embodiment, a lactose derivative of formula 7

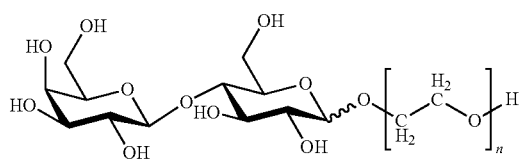
7 wherein n is as defined above.

Preferably, in a compound of formula 6 moiety X is a group of formula 1a, 1b or 1c as defined above, thus to form a compound of formula 6a, 6b or 6c, respectively,

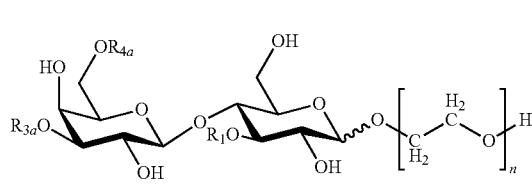
6a

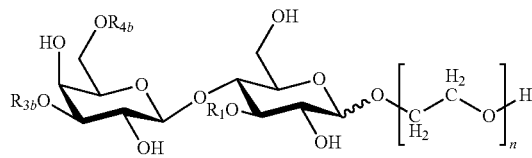
6b

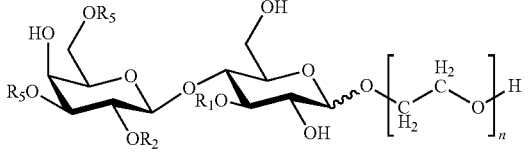
6c wherein R₁, R₂, R₃ₐ, R₃ᵦ, R₄ₐ, R₄ᵦ, R₅ and n are as defined above.

More preferably, the compounds according to formulae 6a, 6b and 6c are human milk oligosaccharide (HMO) glycosyl groups.

Also more preferably, the compound of formula 6a has a glycosyl residue of lacto-N-neotetraose, para-lacto-N-hexaose, para-lacto-N-neohexaose, lacto-N-neohexaose, para-lacto-N-octaose or lacto-N-neooctaose optionally substituted with one or more sialyl and/or fucosyl residue, and the compound of formula 6b has a glycosyl residue of lacto-N-tetraose, lacto-N-hexaose, lacto-N-octaose, iso-lacto-N-octaose, lacto-N-decaose or lacto-N-neodecaose optionally substituted with one or more sialyl and/or fucosyl residue. Even more preferably, the glycosyl residue of compounds according to subformulae 6a, 6b or 6c may be selected from the group of: a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, more preferably from the group of a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose and lacto-N-neotetraose, or salts thereof. The glycosides may be alpha or beta-anomers, but preferably beta-anomers. Especially is preferred a compound of formula 6d

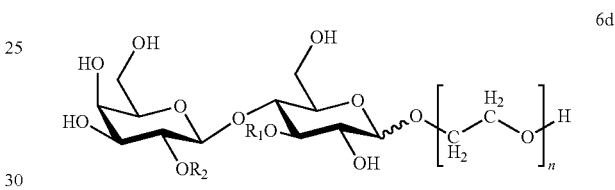
6d wherein R₁ is fucosyl or H, R₂ is fucosyl or H, and n is 2-6, provided that at least one of the R₁ and R₂ groups is fucosyl.

According to another preferred realization of the invention, the glycoconjugate obtainable by the method is an oligosaccharide covalently linked to an α,β-unsaturated amido group as described by the seventh particular embodiment above. Preferably, the glycoconjugate covalently linked to an α,β-unsaturated amido group, obtainable by the seventh particular embodiment, is characterized by formula 8

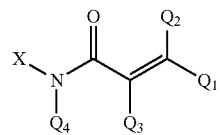
8 wherein X is the moiety of formula 1 as defined above, and Q₁, Q₂, Q₃ and Q₄ are as defined above, by culturing, as disclosed in the seventh particular embodiment, a lactose derivative of formula 9

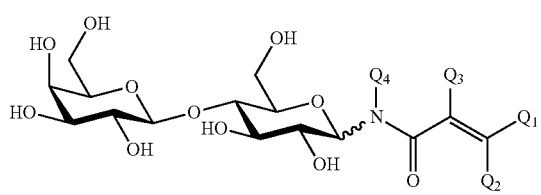
9 wherein Q₁, Q₂, Q₃ and Q₄ are as defined above.

Preferably, in a compound of formula 8 moiety X is a group of formula 1a, 1b or 1c as defined above, thus to form a compound of formula 8a, 8b or 8c, respectively,

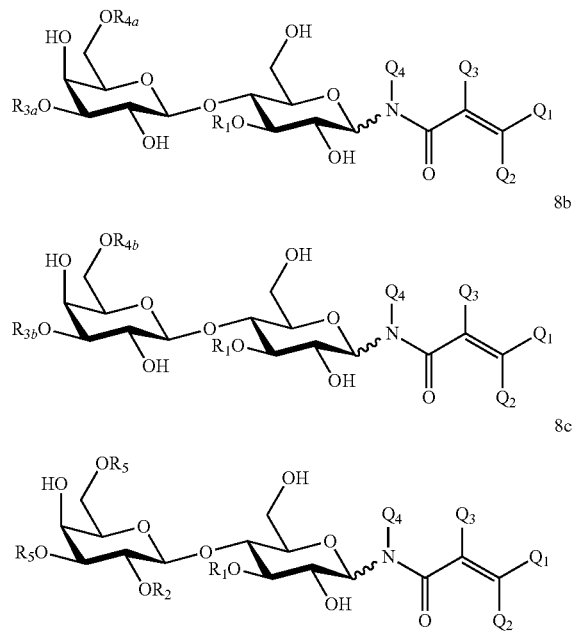

wherein $R_1$, $R_2$, $R_{3a}$, $R_{3b}$, $R_{4a}$, $R_{4b}$, $R_5$, $Q_1$, $Q_2$, $Q_3$ and $Q_4$ are as defined above.

More preferably, the compounds according to formulae 8a, 8b and 8c are human milk oligosaccharide (HMO) glycosyl groups.

Also more preferably, the compound of formula 8a has a glycosyl residue of lacto-N-neotetraose, para-lacto-N-hexaose, para-lacto-N-neohexaose, lacto-N-neohexaose, para-lacto-N-octaose or lacto-N-neooctaose optionally substituted with one or more sialyl and/or fucosyl residue, and the compound of formula 8b has a glycosyl residue of lacto-N-tetraose, lacto-N-hexaose, lacto-N-octaose, iso-lacto-N-octaose, lacto-N-decaose or lacto-N-neodecaose optionally substituted with one or more sialyl and/or fucosyl residue. Even more preferably, the glycosyl residue of compounds according to subformulae 8a, 8b or 8c may be selected from the group of: a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, more preferably from the group of a glycosyl residue of 2'-fucosyllactose, 3-fucosyllactose, 2',3-difucosyllactose, 3'-sialyllactose, 6'-sialyllactose, 3'-sialyl-3-fucosyllactose, lacto-N-tetraose and lacto-N-neotetraose, or salts thereof. The glycosides may be alpha or beta-anomers, but preferably beta-anomers. Especially is preferred a compound of formula 8d wherein $R_1$ is fucosyl or H, $R_2$ is fucosyl or H, provided that at least one of the $R_1$ and $R_2$ groups is fucosyl.

EXAMPLES

Example 1—Tetraethylene glycol 2,3,6,2,3,4,6'-hepta-O-acetyl-β-lactoside

A) To a solution of 2,3,6,2',3',4',6'-hepta-O-acetyl-α-lactosyl bromide (15.0 g) and tetraethylene glycol (13.23 ml) in CH$_2$Cl$_2$ (200 ml) Ag$_2$CO$_3$ (5.90 g) was added at 0° C. under N$_2$. The reaction mixture was stirred at it overnight then filtered through a pad of celite, the filtrate was washed with water and brine, dried and evaporated. The residue was purified by flash chromatography on silica gel to afford the title compound (12.66 g, 72.5%) as a white foam. $^1$H NMR (300 MHz, CDCl$_3$) δ 5.31 (d, J=3.4 Hz, 1H), 5.17 (t, J=9.3 Hz, 1H), 5.08 (dd, J=7.8, 10.4 Hz, 1H), 4.94-4.83 (m, 2H), 4.56 (d, J=7.9, 1H), 4.48-4.44 (m, 2H), 4.14-4.01 (m, 3H), 3.91-3.82 (m, 2H), 3.80-3.73 (m, 1H), 3.72-3.66 (m, 3H), 3.65-3.57 (m, 14H), 2.12 (s, 3H), 2.09 (s, 3H), 2.03 (s, 3H), 2.02 (s, 3H), 2.01 (s, 3-H), 2.01 (s, 3H), 1.94 (s, 3H).

B) To a solution of lactose peracetate (67.8 g) and tetraethylene glycol (69 ml) in CH$_2$Cl$_2$ (500 ml) BF$_3$.OEt$_2$ (64 ml) was added dropwise at 0° C. under Ar. The reaction mixture was stirred at rt overnight. The mixture was neutralised with triethyl amine, diluted with CH$_2$Cl$_2$, washed with saturated NaHCO$_3$ solution and brine, dried and evaporated. The residue was chromatographed in silica gel to give the title compound (50 g, 62%).

Example 2—Tetraethylene glycol β-lactoside

To a solution of tetraethylene glycol 2,3,6,2',3',4',6'-hepta-O-acetyl-β-lactoside (12.66 g) in MeOH (60 ml) MeONa (25% in MeOH, 0.355 ml) was added at 0° C. The reaction mixture was stirred at 0° C. for 3 h then neutralized with acidic resin, filtered and concentrated to afford the title compound (7.88 g, 97.5%) as a white foam. $^1$H NMR (300 MHz, MeOD) δ 4.36 (d, J=7.3 Hz, 1H), 4.35 (d, J=7.8 Hz, 1H), 4.00 (ddd, J=2.9, 4.9, 9.6 Hz, 1H), 3.87 (dd, J=3.3, 9.5 Hz, 1H), 3.82-3.81 (m, 1H), 3.78 (t, J=3.6 Hz, 1H), 3.75-3.74 (m, 1H), 3.72-3.68 (m, 4H), 3.67-3.64 (m, 10H), 3.61-3.55 (m, 5H), 3.53-3.50 (m, 2H), 3.44-3.89 (m, 1H), 3.30-3.24 (m, 1H); $^{13}$C NMR (75 MHz, MeOD) δ 105.0, 104.3, 80.5, 77.0, 76.4, 76.2, 74.8, 74.7, 73.6, 72.5, 71.5, 71.4, 71.4, 71.4, 71.3, 70.3, 69.7, 62.5, 62.2, 61.9.

Example 3—Tetraethylene glycol β-glycoside of 2'-FL

Plasmids and strain, suitable for performing the fermentation, were constructed, and the techniques with regard to cloning were performed in accordance with WO 01/04341 and Drouillard et al. Angew. Chem. Int. Ed. Eng. 45, 1778 (2006), where the general culturing conditions have also been described. Engineered E. coli used in this example was constructed from *E. coli* K12 strain by deleting genes that are liable to degrade the acceptor, the oligosaccharide product and its metabolic intermediates, inter alia the lacZ, lacA and wcaJ genes, maintaining manB, manC, gmd and wcaG genes involved in the GDP-fucose biosynthesis, and inserting *H. pylori* futC gene for α-1,2-fucosyl transferase.

The culture was carried out in a 1 l fermenter containing 0.75 l of mineral culture medium (Samain et al. *J. Biotechnol.* 72, 33 (1999)). The temperature was kept at around 33° C. and the pH regulated at 6.8 with aqueous $NH_4OH$ solution. The inoculum (1% of the volume of the basal medium) consisted in a LB medium and the culture of the producing strain. The exponential growth phase started with the inoculation and stopped until exhaustion of the carbon source (glucose 17.5 g/l) initially added to the medium. Tetraethylene glycol β-lactoside (5.95 g dissolved in 50 ml of water) and the inducer (IPTG, 1-2 ml of a 50 mg/ml solution) were added at the end of the exponential phase. Then a fed-batch was realized, using a 500 g/l aqueous glycerol solution, with a high substrate feeding rate of ≈4.5 g/h of glycerol for 1 l of culture for 5-6 hours followed by a lower glycerol feeding rate of ≈3 g/h for 1 l culture for 20 hours.

At the end of the fermentation, the culture was centrifuged for 20-30 min at 6000 rpm at 25° C. The supernatant was kept. The cells were acidified to pH≈3 using a $H^+$ form resin or treated in water at 80-100° C. for 20-30 min. This resulted in the precipitation of the proteins. The resin was recovered by decantation and precipitated proteins were removed by centrifugation for 20-30 min at 6000 rpm at 25° C. The combined supernatants were subjected to standard chromatographic techniques to give the title compound (4.8 g).

LC-MS (instrument: Bruker microQT of II MS coupled with Dionex Ultimate 3000 UHPLC; ionization: ESI negative, dry temperature: 200° C.; mode: LC-MS, 1:1 split of flow; calibration: with Na-format cluster solution): 663.2744 Da $[M-H]^-$. $^1H$ NMR (300 MHz, $D_2O$) δ 5.29 (brs, 1H, H-1"), 4.48 (ddd, J=11.7, 7.8, 1.9 Hz, 2H), 4.21 (td, J=7.5, 5.7 Hz, 1H), 4.10-3.48 (m, 29H), 3.48-3.40 (m, 1H), 3.33 (ddd, J=9.5, 7.9, 1.9 Hz, 1H), 1.21 (dd, J=6.6, 1.9 Hz, 3H, H-6"). $^{13}C$ NMR (75 MHz, $D_2O$) δ 102.4, 100.4 and 99.5 (C-1, C-1' and C-1"), 76.4, 76.0, 75.4, 75.3, 74.3, 73.7, 73.0, 71.8, 69.8, 69.7, 69.6, 69.5, 69.2, 68.9, 68.3, 67.0, 61.2, 60.4, 60.3, 15.4 (C-6").

Example 4—Octyl β-glycoside of 2'-FL

The culture was carried out as described in Example 3 with the following differences:
the starting volume of the mineral culture medium was 0.5 l,
the acceptor was octyl β-lactoside (5 g, ref.) which was added as neat material to the medium at the end of the exponential phase,
glycerol feeding lasted 93 hours.
The course of the fermentation was followed by LC-MS. A new compound was detected at 599.2937 Da $[M-H]^-$, corresponding to the title product (for LC-MS conditions see Example 3). The acceptor/product ratio measured is given in the following table:

|  | 20 hours | 93 hours |
| --- | --- | --- |
| supernatant | 66/34 | 34/66 |
| intracellular | 48/52 | 7/93 |

The culture was centrifuged for 20-30 min at 6000 rpm at 25° C. The supernatant was acidified to pH≈3 using a $H^+$ form resin or treated in water at 80-100° C. for 20-30 min. The resin was recovered by decantation and precipitated proteins were removed by centrifugation for 20-30 min at 6000 rpm at 25° C. A part of the supernatant was subjected to standard chromatographic techniques to give the title compound, the $^1H$-NMR spectrum of which was in good agreement with that reported in Meloncelli et al. *Aust. J. Chem.* 62, 558 (2009).

Example 5—O-L-serine-β-glycoside of 2'-FL

The culture was carried out as described in Example 4 with the following difference:
the acceptor was O-β-lactosyl-L-serine (5 g, Rude et al. *Carbohydr. Res.* 8, 219 (1968)) which was dissolved in water and added to the medium at the end of the exponential phase,
glycerol feeding lasted 48 hours.
The course of the fermentation was followed by LC-MS. A new compound was detected at 574.1916 Da $[M-H]^-$, corresponding to the title product (for LC-MS conditions see Example 3). After 22 hours from its addition practically no acceptor could be detected in the intracellular matrix and the supernatant.

Example 6—N-acryl-β-N-glycoside of 2'-FL

The culture was carried out as described in Example 4 with the following difference:
the acceptor was N-acryl-β-lactosyl-amine (5 g, Kallin et al. *J. Carbohydr. Chem.* 8, 597 (1989)) which was added as neat material to the medium at the end of the exponential phase,
glycerol feeding lasted 94 hours.
The course of the fermentation was followed by LC-MS. A new compound was detected at 540.1933 Da $[M-H]^-$, corresponding to the title product (for LC-MS conditions see Example 3). The acceptor/product ratio measured is given in the following table:

|  | 21 hours | 94 hours |
| --- | --- | --- |
| supernatant | 52/48 | 24/76 |
| intracellular | 34/66 | 22/78 |

The invention claimed is:
1. A method for producing a glycoconjugate comprising an oligosaccharide part covalently linked to a polyethylene glycol, the method comprising:
(i) providing a genetically modified cell comprising a gene encoding a glycosyl transferase enzyme that is able to transfer the glycosyl residue of an activated sugar nucleotide to an internalized acceptor and a gene encoding the *E. coli* lactose permease,
(ii) culturing said genetically modified cell in the presence of an exogenous acceptor according to formula 7

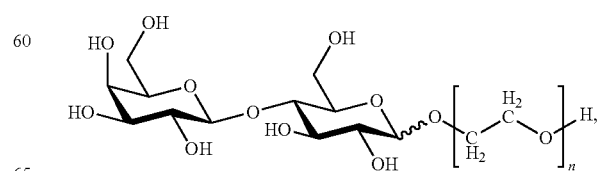

wherein n is an integer from 2 to 6, inducing
   (a) internalization of the exogenous acceptor by the genetically modified cell, and
   (b) formation of said glycoconjugate from said internalized acceptor molecule by a glycosyl transfer mediated by said glycosyl transferase enzyme expressed by said cell, and then
   (iii) collecting said glycoconjugate from the fermentation broth.

2. The method according claim 1, wherein said genetically modified cell provided in step (i) further comprises a set of genes encoding enzymes responsible for the synthesis of said activated sugar nucleotide by a de novo pathway, and wherein said culturing step (ii) further induces producing said activated sugar nucleotide by a de novo pathway.

3. The method according to claim 1, wherein said glycosyl transferase enzyme is selected from the group consisting of N-acetyl-glucosaminyl transferases, galactosyl transferases, N-acetyl-galactosaminyl transferases, glucuronosyl transferases, sialyl transferases and fucosyl transferases.

4. The method according to claim 3, wherein said glycosyl transferase enzyme is α-1,2-fucosyl transferase.

5. The method according to claim 3, wherein said glycosyl transferase enzyme is selected from the group consisting of β-1,3-N-acetyl-glucosaminyl transferase, β-1,6-N-acetyl-glucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4-fucosyl transferase.

6. The method according to claim 1, wherein the genetically modified cell is a bacterium or yeast.

7. The method according to claim 1, wherein the genetically modified cell is *E. coli* of LacZ⁻, LacY⁺ genotype, the exogenous acceptor is a lactose covalently linked to a polyethylene glycol, the glycosyl transferase is a fucosyl transferase, and/or a sialyl transferase, and/or an N-acetylglucosaminyl transferase and/or a galactosyl transferase, and the glycoconjugate produced by the method is a fucosylated and/or sialylated and/or N-acetylglucosaminylated and/or galactosylated lactose covalently linked to a polyethylene glycol.

8. The method according to claim 7, wherein the exogenous acceptor consists of lactose covalently linked to said polyethylene glycol and the glycoconjugate is a fucosylated lactose covalently linked to polyethylene glycol.

9. The method according to claim 7, wherein the oligosaccharide part of the glycoconjugate is a human milk oligosaccharide.

10. The method according to claim 9, wherein the human milk oligosaccharide is selected from the group consisting of 2'-fucosyllactose, 3-fucosyllactose, difucosyllactose, 3'-sialyllactose, 6'-sialyllactose, 3'-sialyl-3-fucosyllactose, lacto-N-tetraose (LNT) and lacto-N-neotetraose (LNnT).

11. The method according to claim 8, wherein the glycoconjugate is a compound of formula 7a

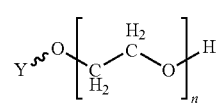

wherein Y is a human milk oligosaccharide glycosyl residue, and n is an integer from 2-6.

12. The method according to claim 11, wherein n is an integer of from 2 to 4.

13. The method according to claim 11, wherein the compound of formula 7a is of formula 8d

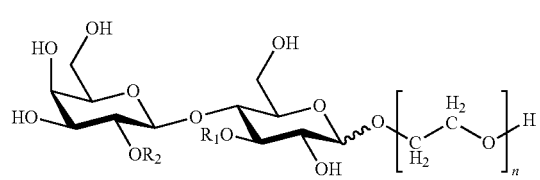

wherein $R_1$ is fucosyl or H, $R_2$ is fucosyl or H, n is an integer from 2 to 6, provided that at least one of the $R_1$ and $R_2$ groups is fucosyl.

14. The method according to claim 13, wherein n is an integer of from 2 to 4.

* * * * *